(12) United States Patent
Oliver

(10) Patent No.: US 11,274,341 B2
(45) Date of Patent: Mar. 15, 2022

(54) ASSAY METHODS USING DNA BINDING PROTEINS

(75) Inventor: John S. Oliver, Bristol, RI (US)

(73) Assignee: NABsys, 2.0 LLC, Providence, RI (US)

( * ) Notice: Subject to any disclaimer, the term of this patent is extended or adjusted under 35 U.S.C. 154(b) by 0 days.

(21) Appl. No.: 13/370,874

(22) Filed: Feb. 10, 2012

(65) Prior Publication Data

US 2012/0214162 A1 Aug. 23, 2012

Related U.S. Application Data

(60) Provisional application No. 61/441,945, filed on Feb. 11, 2011.

(51) Int. Cl.
| | |
|---|---|
| C12Q 1/68 | (2018.01) |
| C12Q 1/6869 | (2018.01) |
| C12Q 1/6816 | (2018.01) |
| C07H 21/02 | (2006.01) |

(52) U.S. Cl.
CPC ......... *C12Q 1/6869* (2013.01); *C12Q 1/6816* (2013.01)

(58) Field of Classification Search
None
See application file for complete search history.

(56) References Cited

U.S. PATENT DOCUMENTS

| | | | |
|---|---|---|---|
| 3,699,437 A | 10/1972 | Ur | |
| H201 H | 1/1987 | Yager | |
| 4,810,650 A | 3/1989 | Kell et al. | |
| 4,874,499 A | 10/1989 | Smith et al. | |
| 5,194,133 A | 3/1993 | Clark et al. | |
| 5,202,231 A | 4/1993 | Drmanac et al. | |
| 5,246,552 A | 9/1993 | Kamiya et al. | |
| 5,314,829 A | 5/1994 | Coles | |
| 5,405,519 A | 4/1995 | Schwartz | |
| 5,427,663 A | 6/1995 | Austin et al. | |
| 5,455,166 A | 10/1995 | Walker | |
| 5,539,082 A | 7/1996 | Nielsen et al. | |
| 5,560,811 A | 10/1996 | Briggs et al. | |
| 5,599,664 A | 2/1997 | Schwartz | |
| 5,650,305 A * | 7/1997 | Hui et al. ...................... 435/450 | |
| 5,681,947 A | 10/1997 | Bergstrom et al. | |
| 5,683,881 A | 11/1997 | Skiena | |
| 5,720,928 A | 2/1998 | Schwartz | |
| 5,744,699 A | 4/1998 | Suzuki | |
| 5,773,571 A | 6/1998 | Nielsen et al. | |
| 5,795,782 A | 8/1998 | Church et al. | |
| 5,824,477 A | 10/1998 | Stanley | |
| 5,837,115 A | 11/1998 | Austin et al. | |
| 5,877,280 A * | 3/1999 | Wetmur ............... C07K 14/195 435/6.11 | |
| 5,908,745 A | 6/1999 | Mirzabekov et al. | |
| 5,928,869 A | 7/1999 | Nadeau et al. | |
| 5,942,391 A | 8/1999 | Zhang et al. | |
| 5,972,619 A | 10/1999 | Drmanac et al. | |
| 6,015,714 A | 1/2000 | Baldarelli et al. | |
| 6,020,599 A | 2/2000 | Yeo | |
| 6,025,891 A | 2/2000 | Kim | |
| 6,084,648 A | 7/2000 | Yeo | |
| 6,096,503 A | 8/2000 | Sutcliffe et al. | |
| 6,100,949 A | 8/2000 | Kim | |
| 6,108,666 A | 8/2000 | Floratos et al. | |
| 6,124,092 A * | 9/2000 | O'Neill ............... C12Q 1/6874 435/6.11 | |
| 6,128,051 A | 10/2000 | Kim et al. | |
| 6,147,198 A | 11/2000 | Schwartz | |
| 6,150,089 A | 11/2000 | Schwartz | |
| 6,174,671 B1 | 1/2001 | Anantharaman et al. | |
| 6,182,733 B1 | 2/2001 | McReynolds | |
| 6,210,891 B1 | 4/2001 | Nyren et al. | |
| 6,210,896 B1 | 4/2001 | Chan | |
| 6,258,568 B1 | 7/2001 | Nyren | |
| 6,263,286 B1 | 7/2001 | Gilmanshin et al. | |
| 6,267,872 B1 | 7/2001 | Akeson et al. | |
| 6,270,965 B1 | 8/2001 | Kleiber et al. | |
| 6,274,320 B1 | 8/2001 | Rothberg et al. | |
| 6,294,136 B1 | 9/2001 | Schwartz | |
| 6,294,325 B1 * | 9/2001 | Wetmur ............... C07K 14/195 435/6.1 | |
| 6,303,288 B1 | 10/2001 | Furcht et al. | |
| 6,304,318 B1 | 10/2001 | Matsumoto | |
| 6,340,567 B1 | 1/2002 | Schwartz et al. | |
| 6,355,420 B1 | 3/2002 | Chan | |
| 6,362,002 B1 | 3/2002 | Denison et al. | |
| 6,392,719 B2 | 5/2002 | Kim | |
| 6,400,425 B1 | 6/2002 | Kim et al. | |
| 6,403,311 B1 | 6/2002 | Chan | |
| 6,410,243 B1 | 6/2002 | Wyrick et al. | |
| 6,413,792 B1 | 7/2002 | Sauer et al. | |

(Continued)

FOREIGN PATENT DOCUMENTS

| | | |
|---|---|---|
| DE | 19936302 A1 | 2/2001 |
| EP | 455508 A1 | 11/1991 |

(Continued)

OTHER PUBLICATIONS

"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"List of sequenced bacterial genomes" (Wikipedia.com; accessed Jan. 24, 2014).*

(Continued)

*Primary Examiner* — Bradley L. Sisson
(74) *Attorney, Agent, or Firm* — Goodwin Procter LLP

(57) ABSTRACT

Assay methods for preparing a biomolecule analyte includes hybridizing a sequence specific oligonucleotide probe to a biomolecule template and reacting the resulting analyte with a binding moiety.

23 Claims, 17 Drawing Sheets

Specification includes a Sequence Listing.

(56) References Cited

U.S. PATENT DOCUMENTS

| | | |
|---|---|---|
| 6,428,959 B1 | 8/2002 | Deamer |
| 6,448,012 B1 | 9/2002 | Schwartz |
| 6,464,842 B1 | 10/2002 | Golovchenko et al. |
| 6,497,138 B1 | 12/2002 | Abdel-Rahman et al. |
| 6,503,409 B1 | 1/2003 | Fleming |
| 6,509,158 B1 | 1/2003 | Schwartz |
| 6,537,755 B1 | 3/2003 | Drmanac |
| 6,537,765 B2 | 3/2003 | Stricker-Kongra et al. |
| 6,610,256 B2 | 8/2003 | Schwartz |
| 6,616,895 B2 | 9/2003 | Dugas et al. |
| 6,617,113 B2 | 9/2003 | Deamer |
| 6,627,067 B1 | 9/2003 | Branton et al. |
| 6,672,067 B2 | 1/2004 | Farmer et al. |
| 6,673,615 B2 | 1/2004 | Denison et al. |
| 6,685,841 B2 | 2/2004 | Lopez et al. |
| 6,689,563 B2 | 2/2004 | Preparata et al. |
| 6,696,022 B1 | 2/2004 | Chan et al. |
| 6,706,203 B2 | 3/2004 | Barth et al. |
| 6,713,263 B2 | 3/2004 | Schwartz |
| 6,723,513 B2 | 4/2004 | Lexow |
| 6,746,594 B2 | 6/2004 | Akeson et al. |
| 6,762,059 B2 | 7/2004 | Chan et al. |
| 6,772,070 B2 | 8/2004 | Gilmanshin et al. |
| 6,783,961 B1 * | 8/2004 | Edwards ............... C07K 14/47 |
| | | 435/91.1 |
| 6,790,671 B1 | 9/2004 | Austin et al. |
| 6,818,395 B1 | 11/2004 | Quake et al. |
| 6,887,714 B2 | 5/2005 | Fritsch et al. |
| 6,905,586 B2 | 6/2005 | Lee et al. |
| 6,911,345 B2 | 6/2005 | Quake et al. |
| 6,919,002 B2 | 7/2005 | Chopra |
| 6,927,065 B2 | 8/2005 | Chan et al. |
| 6,936,433 B2 | 8/2005 | Akeson et al. |
| 6,952,651 B2 | 10/2005 | Su |
| 7,001,792 B2 | 2/2006 | Sauer et al. |
| 7,005,264 B2 | 2/2006 | Su et al. |
| 7,034,143 B1 | 4/2006 | Preparata et al. |
| 7,071,324 B2 | 7/2006 | Preparata et al. |
| 7,118,657 B2 | 10/2006 | Golovchenko et al. |
| 7,170,050 B2 | 1/2007 | Turner et al. |
| 7,176,007 B2 | 2/2007 | Cox et al. |
| 7,189,503 B2 | 3/2007 | Akeson et al. |
| 7,211,414 B2 | 5/2007 | Hardin et al. |
| 7,217,562 B2 | 5/2007 | Cao et al. |
| 7,238,485 B2 | 7/2007 | Akeson et al. |
| 7,248,771 B2 | 7/2007 | Schmidt et al. |
| 7,250,115 B2 | 7/2007 | Barth |
| 7,257,987 B2 | 8/2007 | O'Brien et al. |
| 7,259,342 B2 | 8/2007 | Lin et al. |
| 7,262,859 B2 | 8/2007 | Larson et al. |
| 7,279,337 B2 | 10/2007 | Zhu |
| 7,282,130 B2 | 10/2007 | Flory |
| 7,282,330 B2 | 10/2007 | Zhao et al. |
| 7,297,518 B2 | 11/2007 | Quake et al. |
| 7,302,146 B2 | 11/2007 | Turner et al. |
| 7,315,019 B2 | 1/2008 | Turner et al. |
| 7,329,492 B2 | 2/2008 | Hardin et al. |
| 7,351,538 B2 | 4/2008 | Fuchs et al. |
| 7,355,216 B2 | 4/2008 | Yang et al. |
| 7,371,520 B2 | 5/2008 | Zhao et al. |
| 7,402,422 B2 | 7/2008 | Fuchs et al. |
| 7,432,365 B1 * | 10/2008 | O'Donnell ............. C07K 14/31 |
| | | 435/199 |
| 7,462,449 B2 | 12/2008 | Quake |
| 7,468,271 B2 | 12/2008 | Golovchenko et al. |
| 7,476,503 B2 | 1/2009 | Turner et al. |
| 7,476,504 B2 | 1/2009 | Turner |
| 7,501,245 B2 | 3/2009 | Quake et al. |
| 7,595,160 B2 | 9/2009 | White et al. |
| 7,625,706 B2 | 12/2009 | Akeson et al. |
| 7,670,770 B2 | 3/2010 | Chou et al. |
| 7,678,562 B2 | 3/2010 | Ling |
| 7,731,826 B2 | 6/2010 | Hibbs et al. |
| 7,744,816 B2 | 6/2010 | Su et al. |
| 7,854,435 B2 | 12/2010 | Campbell |
| 7,867,782 B2 | 1/2011 | Barth |
| 7,897,344 B2 | 3/2011 | Dahl et al. |
| 7,939,259 B2 | 5/2011 | Kokoris et al. |
| 8,003,319 B2 | 8/2011 | Polonsky et al. |
| 8,133,719 B2 | 3/2012 | Drmanac et al. |
| 8,232,055 B2 | 7/2012 | Bruhn et al. |
| 8,246,799 B2 | 8/2012 | Oliver et al. |
| 8,262,879 B2 | 9/2012 | Oliver |
| 8,278,050 B2 | 10/2012 | Bailey et al. |
| 8,377,039 B2 | 2/2013 | Utterberg et al. |
| 8,455,260 B2 | 6/2013 | Goldstein et al. |
| 8,507,197 B2 | 8/2013 | Palaniappan |
| 8,715,933 B2 | 5/2014 | Oliver |
| 8,882,980 B2 | 11/2014 | Ling et al. |
| 8,926,813 B2 | 1/2015 | Oliver |
| 9,650,668 B2 | 5/2017 | Oliver et al. |
| 9,702,003 B2 | 7/2017 | Goldstein |
| 9,749,980 B2 | 8/2017 | Girardeau et al. |
| 2001/0039014 A1 * | 11/2001 | Bass ................... B01J 19/0046 |
| | | 435/6.11 |
| 2002/0028458 A1 | 3/2002 | Lexow |
| 2002/0055109 A1 * | 5/2002 | Thill .................... C12Q 1/6809 |
| | | 435/6.15 |
| 2002/0061588 A1 | 5/2002 | Jacobson et al. |
| 2002/0127855 A1 | 9/2002 | Sauer et al. |
| 2002/0131902 A1 | 9/2002 | Levy |
| 2002/0150961 A1 | 10/2002 | Bogyo et al. |
| 2003/0003609 A1 | 1/2003 | Sauer et al. |
| 2003/0064095 A1 | 4/2003 | Martin et al. |
| 2003/0104428 A1 | 6/2003 | Branton et al. |
| 2003/0143614 A1 | 7/2003 | Drmanac |
| 2003/0186256 A1 | 10/2003 | Fischer |
| 2003/0208165 A1 | 11/2003 | Christensen et al. |
| 2004/0137734 A1 | 7/2004 | Chou et al. |
| 2004/0146430 A1 | 7/2004 | Dugas |
| 2005/0019784 A1 | 1/2005 | Su et al. |
| 2005/0202444 A1 | 9/2005 | Zhu |
| 2006/0024678 A1 * | 2/2006 | Buzby .................. C12Q 1/6869 |
| | | 435/6.1 |
| 2006/0025419 A1 * | 2/2006 | Richmond ........... A61K 31/498 |
| | | 514/250 |
| 2006/0154399 A1 | 7/2006 | Sauer et al. |
| 2006/0269483 A1 | 11/2006 | Austin et al. |
| 2006/0287833 A1 | 12/2006 | Yakhini |
| 2007/0020772 A1 | 1/2007 | Cao et al. |
| 2007/0039920 A1 | 2/2007 | Kutchoukov et al. |
| 2007/0042366 A1 | 2/2007 | Ling |
| 2007/0054276 A1 | 3/2007 | Sampson |
| 2007/0084163 A1 | 4/2007 | Lai |
| 2007/0178240 A1 | 8/2007 | Yamazaki et al. |
| 2007/0190524 A1 | 8/2007 | Mauclere et al. |
| 2007/0190542 A1 | 8/2007 | Ling et al. |
| 2007/0218471 A1 | 9/2007 | Kim et al. |
| 2007/0231795 A1 | 10/2007 | Su |
| 2007/0238112 A1 | 10/2007 | Sohn et al. |
| 2008/0085840 A1 | 4/2008 | Buzby |
| 2008/0119366 A1 | 5/2008 | Sauer et al. |
| 2008/0153086 A1 * | 6/2008 | Wong .................. C12Q 1/6809 |
| | | 435/6.11 |
| 2008/0242556 A1 | 10/2008 | Cao et al. |
| 2008/0254995 A1 | 10/2008 | Kim et al. |
| 2008/0305482 A1 | 12/2008 | Brentano et al. |
| 2009/0005252 A1 | 1/2009 | Drmanac et al. |
| 2009/0011943 A1 | 1/2009 | Drmanac et al. |
| 2009/0021616 A1 | 1/2009 | Endo |
| 2009/0099786 A1 | 4/2009 | Oliver et al. |
| 2009/0111115 A1 | 4/2009 | Drmanac et al. |
| 2009/0117540 A1 | 5/2009 | Sorge |
| 2009/0136948 A1 | 5/2009 | Han et al. |
| 2009/0214392 A1 | 8/2009 | Kameoka et al. |
| 2009/0299645 A1 | 12/2009 | Colby et al. |
| 2010/0078325 A1 | 4/2010 | Oliver |
| 2010/0096268 A1 | 4/2010 | Ling et al. |
| 2010/0143960 A1 * | 6/2010 | Bazin ........................... 435/29 |
| 2010/0214162 A1 | 8/2010 | Talbot et al. |
| 2010/0243449 A1 | 9/2010 | Oliver |
| 2010/0297644 A1 | 11/2010 | Kokoris et al. |
| 2010/0310421 A1 * | 12/2010 | Oliver ............... G01N 33/48721 |
| | | 422/82.01 |

(56) References Cited

U.S. PATENT DOCUMENTS

| | | | |
|---|---|---|---|
| 2010/0331194 A1* | 12/2010 | Turner | C12Q 1/6869 506/2 |
| 2012/0052079 A1 | 3/2012 | Richardson et al. | |
| 2012/0074925 A1 | 3/2012 | Oliver | |
| 2012/0208193 A1 | 8/2012 | Okino et al. | |
| 2012/0214162 A1 | 8/2012 | Oliver | |
| 2012/0222958 A1 | 9/2012 | Pourmand et al. | |
| 2013/0011934 A1 | 1/2013 | Oliver et al. | |
| 2013/0085473 A1 | 4/2013 | Weilbacher et al. | |
| 2014/0087390 A1 | 3/2014 | Oliver et al. | |
| 2014/0174927 A1 | 6/2014 | Bashir et al. | |
| 2014/0212874 A1 | 7/2014 | Oliver | |
| 2014/0224356 A1 | 8/2014 | Hatton et al. | |

FOREIGN PATENT DOCUMENTS

| | | |
|---|---|---|
| EP | 0958495 A1 | 11/1999 |
| EP | 1486775 A1 | 12/2004 |
| EP | 1685407 A1 | 8/2006 |
| JP | 2002519011 A | 7/2002 |
| JP | 2002526759 A | 8/2002 |
| JP | 2003-028826 A | 1/2003 |
| JP | 2003510034 A | 3/2003 |
| JP | 2003513279 A | 4/2003 |
| JP | 2004004064 A | 1/2004 |
| JP | 2007068413 A | 3/2007 |
| WO | WO-9004652 | 5/1990 |
| WO | WO-9322678 A2 | 11/1993 |
| WO | WO-9617957 | 6/1996 |
| WO | WO-2008069973 | 11/1997 |
| WO | WO-9835012 A2 | 8/1998 |
| WO | WO-0000645 A1 | 1/2000 |
| WO | WO-0009757 | 2/2000 |
| WO | WO-0011220 A1 | 3/2000 |
| WO | WO-0020626 A1 | 4/2000 |
| WO | WO-00022171 | 4/2000 |
| WO | WO-0056937 A2 | 9/2000 |
| WO | WO-0062931 A1 | 10/2000 |
| WO | WO-0079257 A1 | 12/2000 |
| WO | WO-0118246 A1 | 3/2001 |
| WO | WO-0131063 A1 | 5/2001 |
| WO | WO-0133216 A1 | 5/2001 |
| WO | WO-0137958 | 5/2001 |
| WO | WO-0142782 | 6/2001 |
| WO | WO-0146467 A2 | 6/2001 |
| WO | WO-0207199 | 1/2002 |
| WO | WO-02066595 A1 | 8/2002 |
| WO | WO-2003000920 A2 | 1/2003 |
| WO | WO-03010289 | 2/2003 |
| WO | WO-03079416 | 9/2003 |
| WO | WO-03089666 A2 | 10/2003 |
| WO | WO-03106693 | 12/2003 |
| WO | WO-04035211 A1 | 4/2004 |
| WO | WO-04085609 A2 | 10/2004 |
| WO | WO-05017025 | 2/2005 |
| WO | WO-06020775 | 2/2006 |
| WO | WO-06028508 | 3/2006 |
| WO | WO-2006052882 | 5/2006 |
| WO | WO-2007021502 A1 | 2/2007 |
| WO | WO-07/041621 A2 | 4/2007 |
| WO | WO-2007041621 A2 | 4/2007 |
| WO | WO-2007084076 A1 | 7/2007 |
| WO | WO-2007106509 | 9/2007 |
| WO | WO-2007109228 A1 | 9/2007 |
| WO | WO-2007111924 | 10/2007 |
| WO | WO-2007127327 | 11/2007 |
| WO | WO-2008021488 | 2/2008 |
| WO | WO-2008039579 | 4/2008 |
| WO | WO-2008042018 | 4/2008 |
| WO | WO-2008046923 | 4/2008 |
| WO | WO-2008049021 | 4/2008 |
| WO | WO-2008079169 | 7/2008 |
| WO | WO-2009046094 A1 | 4/2009 |
| WO | WO-2010002883 A2 | 1/2010 |
| WO | WO-2010028140 A2 | 3/2010 |
| WO | WO-2010111605 A2 | 9/2010 |
| WO | WO-2010138136 A1 | 12/2010 |
| WO | WO-2011109825 A2 | 9/2011 |
| WO | WO-2012109574 A2 | 8/2012 |
| WO | WO-2013016486 A1 | 1/2013 |
| WO | WO-201 4052433 A2 | 4/2014 |

OTHER PUBLICATIONS

"Human Hybrids," by Michael F. Hammer, Scientific American, May 2013, pp. 66-71. (Year: 2013).*

"Human Hybrids," by Michael F. Hammer, Scientific American, May 2013. (Year: 2013).*

"HIV Integration", Wikipedia.com; accessed Mar. 16, 2019. (Year: 2019).*

Drmanac, R., et al. (2002) "Sequencing by Hybridization (SBH): Advantages, Achievements, and Opportunities," Advances in Biochemical Engineering/Biotechnology, vol. 77: 75-101.

International Preliminary Report on Patentability, Application No. PCT/US2010/028848, dated Sep. 27, 2011, 8 pages.

International Search Report and Written Opinion dated Feb. 5, 2009, PCT/US08/078432.

Invitation to Pay Additional Fees and, Where Applicable, Protest Fee & Partial International Search dated Aug. 19, 2010, PCT/US2010/028848, 7 pages.

Invitation to Pay Additional Fees and, Where Applicable, Protest Fee & Partial International Search dated Jul. 10, 2012, PCT/US2012/024708, 10 pages.

Akeson, et al., "Microsecond time-scale discrimination among polycytidylic acid, polyadenylic acid, and polyuridylic acid as homopolymers or as segments within single RNA molecules," Biophys. J. 77, 3227-3233 (1999).

Alberts, B., et al., (1970) "T4 Bacteriophage Gene 32: A Structural Protein in the Replication and Recombination of DNA," Nature 227:1313-1318.

Amit, B., et al., (1974) "Photosensitive Protecting Groups of Amino Sugars and Their Use in Glycoside Synthesis. 2-Nitrobenzyloxycarbonylamino and 6-Nitroveratryloxycarbonylamino Derivatives," J. Org. Chem. 39:192-196.

Arratia, R., et al., (1989) "Poisson Process Approximation for Repeats in One Sequence and Its Application to Sequencing by Hybridization," Dept. of Mathematics, University of Southern California.

Ashkin, "Optical trapping and manipulation of neutral particles using lasers," Proc. Natl. Acad. Sci. USA, vol. 94, DD. 4853-4860, May 1997.

Austin, M., et al., (2004) "Fabrication of 5 nm Linewidth and 14 nm Pitch Features by Nanoimprint Lithography," App. Phys. Lett. 84:5299-5301.

Bains, W., et al., (1988) "A Novel Method for Nucleic Acid Sequence Determination," J. Theor. Biol. 135:303-307.

Baliga, R., et al., (2001) "Kinetic Consequences of Covalent Linkage of DNA Binding Polyamides," Biochemistry 40:3-8.

Ben-Dor et al, "On the Complexity of Positional Sequencing by Hybridization", Journal of Computational Biology, vol. 8, No. 4, 2001, pp. 361-371.

Bennett et al. Pharmacogenomics (2005) 6:373-382.

Bianco, P., et al., "Interaction of the RecA Protein of *Escherichia coli* with Single-Stranded Oligodeoxyribonucleotides," Nucleic Acids Research vol. 24. No. 24 (1996) 4933-4939.

Bloom, et al, Applications of Numbered Undirected Graphs, Proceedings of the IEEE, vol. 65, No. 4, Apr. 1977, pp. 562-570.

Branton, Daniel et al, "The potential and challenges of anopore sequencing," Nature Biotechnology, vol. 26, No. 10, Oct. 2008, pp. 1146-1153.

Buchmueller, K.L., et al., (2005) "Extending the Language of DNA Molecular Recognition by Polyamides: Unexpected Influence of Imidazole and Pyrrole Arrangement on Binding Affinity and Specificity," J. Am. Chem. Soc. 127:742-750.

Buchmueller, K.L., et. al., (2006) "Physical and Structural Basis for the Strong Interactions of the—ImPy—Central Pairing Motif in the Polyamide f-ImPylm," Biochemistry 45:13551-13565.

(56) References Cited

OTHER PUBLICATIONS

Cao, H., et al., (2002) "Fabrication of 10 nm Enclosed Nanofluidic Channels," Applied Physics Letters 81(1): 174-176.
Cao, H., et al., (2002) "Gradient Nanostructures for Interfacing Microfluidics and Nanofluidics," Applied Physics Letters 81:3058-3060.
Chen, C., et al., (1994) "Analogous Organic Synthesis of Small-Compound Libraries: Validation of Combinatorial Chemistry in Small-Molecule Synthesis," J. Am. Chem. Soc. 116:2661-2662.
Chen, P., et al., (2004) "Probing Single DNA Molecule Transport Using Fabricated Nanopores," Nano Letters 4:2293-2298.
Chetverin, A., et al., (1994) "Oligonucleotide Arrays: New Concepts and Possibilities," Bio/Technology 12:1093-1099.
Cox, M. (2007) "Motoring Along with the Bacterial RecA Protein," Nature Reviews—Molecular Cell Biology 9:127-138.
Dervan, P.B. (2001) "Molecular Recognition of DNA by Small Molecules," Bioorg. Med. Chem. 9:2215-2235.
Dervan, P.B., et al., (2003) "Recognition of the DNA minor groove by pyrrole-imidazole polyamides," Curr. Op. Struc. Biol. 13:284-299.
Doss, R.M., et al., (2006) "Programmable Oligomers for Minor Groove DNA Recognition," J. Am. Chem. Soc. 128:9074-9079.
Drmanac, R., et al. (1989) "Sequencing of Megabase Plus DNA by Hybridization: Theory of the Method," Genomics 4:114-128.
Ellervik, U., et al., (2000) "Hybroxybenzamide/Pyrrole Pair Distinguishes T-A from A-T Base Pairs in the Minor Groove of DNA," J. Am. Chem. Soc. 122:9354-9360.
Farkas, Z., et al., (2003) "DNA Uptake Into Nuclei: Numerical and Analytical Results," J. Phys.: Condens. Matter 15:S1767-S1777.
Fechter, E.J., et al., (2005) "Sequence-specific Fluorescence Detection of DNA by Polyamide-Thiazole Orange Conjugates," J. Am. Chem. Soc. 127:16685-16691.
Floreancig, P.E., et al., (2000) "Recognition of the Minor Groove of DNA by Hairpin Polyamides Containing—Substituted—,—Amino Acids," J. Am. Chem. Soc. 122:6342-6350.
Fodor, S., et al., (2005) "Light-Directed, Spatially Addressable Parall Chemical Synthesis" Research Article 6 pgs.
Fologea, D., et al., (2005) "Slowing DNA Translocation in a Solid-State Nanopore," Nano Lett. 5(9):1734-7.
Frieze, A., et al., (1999) "Optimal Reconstruction of a Sequence From its Probes," 12 pgs.
Gerland, U., et al., (2004) "Translocation of Structured Polynucleotides Through Nanopores," Phys. Biol. 1:19-26.
Gershow, M., et al., (2007) "Recapturing and Trapping Single Molecules with a Solid-State Nanopore," Nature Nanotech. 2:775-779.
Ghosh, et al, Detection of Double-Stranded DNA: molecular methods and applications for DNA diagnostics Molecular Biosystems (2006) vol. 2, pp. 551-560.
Giehart B., et al., (2008) "Nanopore with transverse nanoelectrodes for electrical characterization and sequencing of DNA" Sensors and Actuators B., Elsevier Sequoia S.A, ScienceDirect, 132:2.
Gracheva, M., et al., (2002) "Simulation of the Electric Response of DNA Translocation through a Semiconductor Nanopore-Capacitor," Nanotechnology 17:622-633.
Guo, L. (2004) "Recent Progress in Nanoimprint Technology and its Application," J. Phys. D: Appl. Phys 37:R123-R141 (Appendices B-D).
Gygi, M.P., et al., (2002) "Use of fluorescent sequence-specific polyamides to discriminate human chromosomes by microscopy and flow cytometry," Nucleic Acids Research 30:2790-2799.
Halby, L., et al., (2005) "Functionalized head-to-head hairpin polyamides: Synthesis, double-stranded DNA-binding activity and affinity," Bioorg. Med. Chem. Lett. 15:3720-3724.
Heller, C., (2001) "Principles of DNA Separation with Capillary Electrophoresis," Electrophoresis 22:629-643.
Heng, J., et al., (2004) "Sizing DNA Using a Nanometer-Diameter Pore," Biophysical Journal 87:2905-2911.
Hudson, B., (1999) "An Experimental Study of SBH with Gapped Probes," 50 pgs.
International Preliminary Report on Patentability dated Apr. 7, 2010, PCT/US2008/078432.
International Preliminary Report on Patentability, Application No. PCT/US2009/055878, dated Nov. 29, 2011, 9 pages.
International Preliminary Report on Patentability, issuance of report dated Mar. 8, 2011, Application No. PCT/US2009/055876.
International Search Report and Written Opinion dated Jun. 29, 2010, PCT/US09/055876, 13 pages.
International Search Report and Written Opinion dated Mar. 24, 2010 for PCT/US09/055878, 13 pages.
International Search Report and Written Opinion dated May 2, 2009, PCTUS2008/078432.
International Search Report and Written Opinion dated Sep. 30, 2010, PCT/US2010/028848, 14 pgs.
International Search Report and Written Opinion for PCT/US09/558876 dated Feb. 10, 2010.
International Search Report and Written Opinion, PCT/US2011/059933, dated Feb. 4, 2012.
International Search Report for PCT/US04/04138, dated May 4, 2006, 5 pages.
Jonsson, U., et al., (1991) "Real-Time Biospecific Interaction Analysis Using Surface Plasmon Resonance and a Sensor Chip Technology," BioTechniques, 11:620-627.
Ju et al., Proc. Nat. Acad. Sci. USA (2006) 103:19635-19640.
Kalaugher, L., (2002) "Diffraction Gradient Lithography Aids Nanofluidics," Nanotechweb.org.
Kanehisa, L. (1984) "Use of Statistical Criteria for Screening Potential Homologies in Nucleic Acid Sequences," Nucleic Acids Research 12:203-213.
Kasianowicz et al., "Characterization of Individual Polynucleotide Molecules Using a Membrane Channel," Proc. Nat. Acad. Sci. USA 93:13770-13773 (1996).
Khrapko, K.R., et al., (1989) "An Oligonucleotide Hybridizatioin Approach to DNA Sequencing," FEBS Lett. 256:118-22.
Kim, C., et al., (1992) "Binding Properties of Replication Protein A from Human and Yeast Cells," Mol. and Cell. Bio. 12(7):3050-3059.
Kuo, et al., "Hybrid three-dimensional nanofluidic/microfluidic devices using molecular gates," Sensors and Actuators A, vol. 102 (Oct. 2002):223-233.
Langa, "Self-organized growth of single crystals of nanopores," Applied Physics Letters, AIP, American Institute of Physics, 2003, vol. 82, No. 2, pp. 278-280.
Li et al., "Lon-beam sculpting at nanometre length scales", Nature 412, 166-169 (2001).
Liang, X., et al., (2007) "Single Sub-20 nm wide Centimeter-Long NanoFluidic Channel Fabricated by Novel Nanoimprint Mold Fabrication and Divest Imprinting," Nano Letters 7:3774-3780.
Liang, X., et al., (2008) "Nanogap Detector Inside Nanofluidic Channel for Fast Real Time Label-Free DNA Analysis," Nano Letters 8:1472-76.
Loakes, D., et al., (1994) "5-Nitroindole as an Universal Base Analogue," Nucleic Acids Research 22:4039-4043.
Loakes, D., et al., (1995) "3-Nitropyrrole and 5-Nitroindole as Universal Bases in Primers for DNA Sequencing and PCR," 23:2361-2366.
Lohman, T., et al., (1994) "*Escherichia coli* Single-Stranded DNA-Binding Protein: Multiple DNA-Binding Modes and Cooperatives," Annu. Rev. Biochem. 63:527-70.
Losi, et al., "Time-Resolved Absorption and Photothermal Measurements with Recombinant Sensory Rhodopsin II from Natronobacterium pharaonis," Biophys. J. 77, 3277-3286, Dec. 1999.
Lysov, Y.P., et al., (1988) "Determination of the Nucleotide Sequence of DNA Using Hybridization with Oligonucleotides. A New Method," Dokl. Acad. Nauk SSSR 303:1508-1511 [Article in Russian].
Margulies et al., (2005) Nature 437:376-380.
Marques, M.A., et al., (2004) "Expanding the Repertoire of Heterocycle Ring Pairs for Programmable Minor Groove DNA Recognition," J. Am. Chem. Soc. 126:10339-10349.
McEntee, K., et al. "Binding of the RecA Protein of *Escherichia coli* to Single- and Double-Stranded DNA." J. Biol. Chem. (1981) 256:8835.

(56) References Cited

OTHER PUBLICATIONS

Meller, A., et al., (2000) "Rapid Nanopore Discrimination Between Single Polynucleotide Molecules," PNAS 97:1079-1084.
Meller, et al., "Voltage-driven DNA translocations through a nanopore," Phys. Rev. Lett. 86(15),3435-3438 (2001).
Nice, E., et al., (1993) "Mapping of the Antibody- and Receptor-Binding Domains of Granulocyte Colony-Stimulating Factor Using an Optical Biosensor," Journal of Chromatography 646:159-168.
Nichols, R., et al., (1994) "A Universal Nucleoside for Use at Ambiguous Sites in DNA Primers," Letters to Nature 369:492-493.
Novopashina, D.S., et al., (2005) "Sequence-Specific Conjugates of Oligo(2'-O-methylribonucleotides) and Hairpin Oligocarboxamide Minor-Groove Binders: Design, Synthesis, and Binding Studies with Double-Stranded DNA," Chemistry & Biodiversity 2:936-952.
Optical Tweezers: Introduction to Optical Tweezers, Retrieved Apr. 21, 2010 from http://www.nbi.dk/~tweezer/introduction.htm, pp. 1-5.
Pablo, P.J., et al., (2000) "Absence of dc-Conductivity." Phys. Rev. Lett. 85:4992-4995.
Partial International Search Report dated Feb. 15, 2010 for PCT/US09/055878, 3 pages.
Perry, J., et al., (2005) "Review of Fabrication of Nanochannels for Single Phase Liquid Flow," 3rd Intl. Conference on Microchannels and Minichannels, Paper No. ICMM2005-75104.
Pevzner, P. et al., (1991) "Improved Chips for Sequencing by Hybridization," Journal of Biomolecular Structure & Dynamics 9:399-410.
Pevzner, P., (1989) "1-Tuple DNA Sequencing: Computer Analysis," Journal of Biomolecular Structure & Dynamics 7:63-73.
Powell, M., et al., (1993) "Characetrization of the Pf3 Single-Strand DNA Binding Protein by Circular Dichroism Spectroscopy," Biochemistry 32:12538-12547.
Preparata, F., et al., (1999) "On the Power of Universal Bases in Sequencing by Hybridization," 7 pgs.
Preparata, F.P., et al., (2000) "Sequencing-by-Hybridization at the Information-Theory Bound: An Optimal Algorithm," J. Comp. Biol. 7: 621-630.
Quake et al. Proc. Nat. Acad. Sci. USA (2003) 100:3960-3964.
Riehn, R. et al., (2005) Proc. Nat. Acad. Sci., 102:1012.
Robertson, J., et al., (2007) "Single-Molecule Mass Spectrometry in Solution Using a Solitary Nanopore," PNAS 104:8207-8211.
Rucker, V.C., et al., (2003) "Sequence Specific Fluorescence Detection of Double Strand DNA," J. Am. Chem. Soc. 125:1195-1202.
Sanger, F. et al., (1977) "DNA Sequencing with Chain-Terminating Inhibitors," Proc. Natl. Acad. Sci. USA 12:5463-5467.
Shinohara. Y., et al., (1995) "Use of a Biosensor Based on Surface Plasmon Resonance and Biotinyl Glycans for Analysis of Sugar Binding Specificities of Lectins," J. Biochem, 117:1076-1082.
Singer, E. (2008) "The $100 Genome," Technology Review 4 pgs.
Smeets, R., et al., (2008) "Translocation of RecA-Coated Double-Stranded DNA through Solid-State Nanopores," Nano Letters pp. A-G.
Southern, E.M. (1996) "DNA Chips: Analysing Sequence by Hybridization to Oligonucleotide on a Large Scale," Trends in Genetics 12(3):110-115.
Storm, A., et al., (2005) "Fast DNA Translocation through a Solid-State Nanopore," Nano Letters 5(7):1193-1197.
Storm, et al., "Fabrication of solid-state nanopores with single-nanometre precision," Nature Materials 2,537-540, Aug. 2003.
Strezoska, Z., et al., (1991) "DNA Sequencing by Hybridization: 100 Bases Read by a Non-Gel-Based Method," Proc. Natl. Acad. Sci. USA 88:10089-10093.
Tegenfeldt, J., et al., (2004) "The Dynamics of Genomic-Length DNA Molecules in 100 nm Channels," Proc. Nat. Acad. Sci. USA 101:10979-10983.
Tersoff, "Less is more," Nature 412, 135-136, Jul. 2001.
Terwilliger, T., et al., (1996) "Gene V Protein Dimerization and Cooperativity of Binding to Poly (dA)," Biochemistry 35:16652-16664.
Tucker, P., et al., (1994) "Crystal Structure of the Adenovirus DNA Binding Protein a Hook-On Model for Cooperative DNA Binding," The EMBO Journal 13(13):2994-3002.
Urbach, A.R., (2001) "Toward rules for 1:1 polyamide:DNA recognition," PNAS 98:4343-4348.
Warren, C.L., et al., (2006) "Defining the Sequence-Recognition Profile of DNA-Binding Molecules," PNAS 103:867-872.
Warren, S., (1996) "The Expanding World of Trinucleotide Repeats," Science 271:1374-1375.
Web article (2003) "DNA Combed Into Nanochannels," http://www.nature.com.
Written Opinion dated Jul. 1, 2008, PCT/US06/38748.
Zhang, W., et al., (2006) "Discrimination of Hairpin Polyamides with an Substituted-aminobutyric Acid as a 5'-TG-3' Reader in DNA Minor Groove," J. Am. Chem. Soc. 128:8766-8776.
Zwolak, M., et al., (2008) "Physical Approaches to DNA Sequencing and Detection." Rev. Mod. Phy. 80:141-165 (J).
Austin, Robert, "The art of sucking spaghetti", Nature Publishing Group, Nature Materials, vol. 2, pp. 567-568, Sep. 2003.
Bourdoncle, A., et al., "Quaruplex-Based Molecular Beacons as Tunable DNA Probes", J. Am. Chem. Soc., vol. 128, No. 34, pp. 11094-11105, 2006.
International Search Report and Written Opinion dated Oct. 25, 2012, PCT/US12/024708.
Lennon, Erwan et al., "Evaporative Pumping of Liquid in Nanochannel for Electrical Measurement of a Single Biomolecule in Nanofluidic Format", Proceedings of the 7th IEEE Internation Conference on Nantechnology, Hong Kong, Aug. 2-5, 2007.
Rapley, Ralph, "Enhancing PCR Amplification and Sequencing Using DNA-Binding Proteins", Molecular Biotechnology, vol. 2, pp. 295-298, 1994.
Riccelli, P. V. et al., "Hybridization of single-stranded DNA targets to immobilized complementary DNA probes: comparison of hairpin versus linear capture probes", Oxford University Press, Nucleic Acids Research, vol. 29, No. 4, pp. 996-1004, 2001.
Anderson, P. et al., "Nkx3.1 and Myc crossregulate shared target genes in mouse and human prostate tumorigenesis," J. Clinical Investigation, May 2012, pp. 1907-1919, vol. 122, http://www.jci.orgAnderson, P. et al., "Nkx3.1 and Myc crossregulate shared target genes in mouse and human prostate tumorigenesis," J. Clinical Investigation, May 2012, pp. 1907-1919, vol. 122, http://www.jci.org.
Arrowsmith, C. et al., "Epigenetic protein families: a new frontier for drug discovery," Nature Reviews: Drug Discovery, May 2012, pp. 384-400, vol. 11, Macmillan Publishers Limited.
Examination Report dated Feb. 7, 2013 in European Application No. 10 717 908.7-1240 (4 pages).
Examination Report dated Mar. 4, 2013 in European Application No. 08 835 216.6-1404 (6 pages).
Greer, E. et al., "Histone methylation: a dynamic mark in health, disease and inheritance," Nature Review: Genetics, May 2012, pp. 343-357, vol. 13, Macmillan Publishers Limited.
Hannenhalli S. et al. Comput Appl Biosci (1996) 12 (1): 19-24.
Heyn, H. et al., "DNA methylation profiling in the clinic: applications and challenges," Nature Review: Genetics, Oct. 2012, pp. 679-692, vol. 13, Macmillan Publishers Limited.
International Preliminary Report on Patentability in PCT/US2012/024708 dated Aug. 13, 2013.
International Preliminary Report on Patentability, Application No. PCT/US2011/053274, dated May 28, 2013, 14 pages.
International Preliminary Report on Patentability, Application No. PCT/US2011/059933, dated May 21, 2013, 8 pages.
International Search Report and Written Opinion, PCT/US2011/053274, dated May 2, 2013.
Invitation to Pay Additional Fees and, Where Applicable, Protest Fee & Partial International Search dated Feb. 15, 2013, PCT/US2011/053274, 9 pages.
Koike, Shinji et al., "Investigation into the Degrading Mechanism of Positive Electrodes after Calendar Life Test Using Transmission Electron Microscopy", 214th ECS Meeting, Abstract #569, The Electrochemical Society, Osaka, Japan, 1 page.
Notice of Reasons for Rejection dated Jun. 17, 2013 in Japanese Patent Application No. 2011-525300.

(56) References Cited

OTHER PUBLICATIONS

Notification of the First Office Action dated Sep. 28, 2012 in Chinese Patent Application No. 200980140663.0.
Notification of the Second Office Action dated Apr. 2, 2013 in Chinese Patent Application No. 200980140663.0.
Olasagasti, F.; Lieberman, K. R.; Benner, S.; Cherf, G. M.; Dahl, J. M.; Deamer, D. W.; Akeson, M. *Nat. Nanotechnol.* 2010, 5, 798-806.
Park, P., "ChIP-seq: advantages and challenges of a maturing technology," Nature Reviews: Genetics, Oct. 2009, pp. 669-680, vol. 10, Macmillan Publishers Limited.
Pastor, W. et al., "Genome-wide mapping of 5-hydroxymethylcytosine in embryonic stem cells," Nature, May 19, 2011, pp. 394-397, vol. 473, Macmillan Publishers Limited.
Rapley, Ralph, "Direct Sequencing of PCR Products with DNA-Binding Proteins", Methods in Molecular Biology, vol. 65, Humana Press Inc., Totowa, NJ, pp. 101-104.
Rehrauer, William M. et al., "Alteration of the Nucleoisude Triphosphate (NTP) Catalytic Domain within *Escherichia coli* recA Protein Attenuates NTP Hydrolysis but Not Joint Molecule Formation*", pp. 1292-1297, The Journal of Biological Chemistry, The American Society for Biochemistry and Molecule Biology, Inc., vol. 268, No. 2, Jan. 15, 1993.
Ross-Innes, C. et al., "Differential oestrogen receptor binding is associated with clinical outcome in breast cancer," Nature, Jan. 2012, pp. 389-394, vol. 481, Macmillan Publishers Limited.
Salpea, P. et al., "Postnatal development- and age-related changes in DNA-methylation patterns in the human genome," Nucleic Acids Research, 2012, pp. 6477-6494, vol. 40, No. 14, Oxford University Press.
Shoaib, M. et al., "PUB-NChIP—"in vivo biotinylation" approach to study chromatin in proximity to a protein of interest," Genome Research, 2013, pp. 331-340, vol. 23, Cold Spring Harbor Laboratory Press, www.genome.org.
Van Steensel, B. et al., "Identification of in vivo DNA targets of chromatin proteins using tethered Dam methyltransfarase," Nature Biotechnology, Apr. 2000, pp. 424-428, vol. 18.
Waugh, David S., "Make the most of affinity tags", pp. 316-320, Trends in Biotechnology, Science Direct, vol. 23, No. 6, Jun. 2005.
Broude et al. (1994) Enhanced DNA sequencing by hybridization, Proc. Natl. Acad. Sci. USA, 91, 3072-3076.
Invitation to Pay Additional Fees and, Where Applicable, Protest Fee & Partial International Search dated Mar. 3, 2014, PCT/US2012/061651, 5 pages.
Shim et al., "Detection and Quantification of Methylation in DNA using Solid-State Nanopores", Scientific Reports, www.nature.com, Mar. 11, 2013, pp. 1-8.
Venkatesan et al., "Stacked Graphene-Al2O3 Nanopore Sensors for Sensitive Detection of DNA and DNA-Protein Complexes", www.acsnano.org, vol. 6, No. 1, 2012, pp. 441-450.
Communication dated Oct. 20, 2015 in European Patent Application No. 11 785 507.2, 8 pages.
Decision to Grant dated Aug. 21, 2014 in European Patent Application No. 10 717 908.7-1559.
Examination Report in European Patent Application No. EP 09 748 871.2-1408 dated Sep. 9, 2015 4 pages.
Examination Report in European Patent Application No. EP 09 807 476.8-1554 dated Apr. 1, 2015 6 pages.
Examination Report dated Jun. 11, 2014 in European Patent Application No. 11 785 507.2-1404, 8 pages.
Examination Report dated Jun. 3, 2014 in European Patent Application No. 08 835 216.6, 5 pages.
Examination Report dated Oct. 23, 2014 in European Patent Application No. 11 785 257.4-1404, 6 pages.
Examination Report dated Oct. 29, 2014 in European Patent Application No. 09 748 871.2-1408, 5 pages.
Final Office Action in Japanese Patent Application No. 2014-218935 dated Jan. 4, 2016 one page.

Howorka et al., "Sequence-specific detection of individual DNA strands using engineered nanopores", nature biotechnology, vol. 19, Jul. 2001.
Intention to Grant dated Jun. 26, 2014 in European Patent Application No. 10 717 908.7-1559.
Intention to Grant dated Mar. 25, 2014 in European Patent Application No. 10 717 908.7-1559.
Intention to Grant dated Oct. 20, 2015 in European Patent Application No. 11 785 257.4-1404.
International Preliminary Report on Patentability dated Apr. 9, 2015 in PCT/US2013/061651, 10 pages.
International Preliminary Report on Patentability dated Sep. 24, 2015 in PCT/US2014/021756, 8 pages.
International Search Report and Written Opinion dated Jul. 29, 2014, PCT/US13/061651, 16 pages.
International Search Report and Written Opinion dated Jul. 29, 2014, PCT/US14/021756, 11 pages.
International Search Report and Written Opinion dated Jun. 26, 2014, PCT/US14/011829, 14 pages.
Notice of Final Rejection dated Jul. 2, 2014 in Japanese Patent Application No. 2011-525300.
Notice of Reasons for Rejection in Japanese Patent Application No. 2013-530398 dated Sep. 14, 2015.
Notification of Reexamination in Chinese Patent Application No. 200980140663.0 dated Nov. 25, 2015 19 pages.
Office Action in Japanese Patent Application No. 2014-218935 dated Jul. 27, 2015 2 pages.
Official action in Japanese Patent Application No. 2013-538841 dated Nov. 12, 2015 9 pages.
Stephen et al., "DNA manipulation sorting, and mapping in nanofluidic systems," Chemical Society Reviews, vol. 39, No. 3, Jan. 1, 2010, p. 1133.
Thompson et al., "Detection of Structural Variations Using Nanodetector Positional Sequencing," AGBT Meeting, Feb. 1, 2012.
Thompson et al., "Mapping and sequencing DNA using nanopores and nanodetectors," Electrophoresis, vol. 33, No. 23, Dec. 12, 2012, pp. 3429-3436.
Thompson et al., "Structural Variations Identified Using Solid-State Nanodetectors," Meeting of the American Society for Human Genetics, Nov. 9, 2012.
Vercoutere et al., "Rapid discrimination among individual DNA hairpin molecules at single-nucleotide resolution using an ion channel" nature biotechnology, vol. 19, Mar. 2001.
Wu et al., "On-column conductivity detection in capillary-chip electrophoresis", 2007, 28, 4612-4619.
"About Lock-In Amplifiers" (Stanford Research), last modified Jan. 19, 2004 and accessed Mar. 29, 2016 at http://www.thinksrs.com/downloads/PDFs/ApplicationNotes/AboutLIAS.pdf.
Kasianowicz, et al., "Characterization of individual polynucleotide molecules using a membrane channel," Proc. Natl. Acad. Sci., vol. 93, pp. 13770-13773, Nov. 1996.
Bai, et al., "Passive Conductivity Detection for Capillary Electrophoresis," Analytical Chemistry, vol. 76, 2004, pp. 3126-3131.
Laugere, et al., "On-Chip Contactless Four-Electrode Conductivity Detection for Capillary Electrophoresis Devices," Analytical Chemistry, vol. 75, pp. 306-312, Jan. 2003.
Communication Pursued to Article 94(3) EPC dated Aug. 30, 2016 in European Patent Application No. 14 706 709.4, 3 pages.
Notice of Reasons for Rejection in Japanese Patent Application No. 2013-530398 dated Aug. 25, 2016.
International Preliminary Report and Written Opinion dated Jul. 21, 2015, PCT/US2014/011829, 10 pages.
Decision to Grant dated Mar. 10, 2016 in European Patent Application No. 11785257.4.
Examination Report dated Apr. 25, 2016 in European Patent Application No. 13 792 116.9-1408 6 pages.
Office Action in European Patent Application No. 08 835 216.6 dated Mar. 24, 2016 1 page.
Notice of Allowance in Japanese Patent Application No. 2013-538841 dated Jul. 7, 2016 3 pages.
International Preliminary Report and Written Opinion dated Sep. 25, 2015, PCT/US2014/021756, 8 pages.

(56) References Cited

OTHER PUBLICATIONS

International Preliminary Report and Written Opinion dated Feb. 8, 2016, PCT/US2015/049765, 19 pages.
International Preliminary Report and Written Opinion dated Mar. 23, 2017, PCT/US2015/049765, 13 pages.
Communication Pursuant to Article 94(3) EPC dated Dec. 20, 2016 in European Patent Application No. 14 724 535.1, 4 pages.
Bell, "The polymerase chain reaction," Immunology Today, vol. 10, No. 10, (1989), pp. 351-355.
Communication Pursued to Article 94(3) EPC dated Sep. 18, 2017 in European Patent Application No. 14 706 709.4, 6 pages.
Gardner, et al., "Acyclic and dideoxy terminator preferences denote divergent sugar recognition by archaeon and Taq DNA polymerases," Nucleic Acids Research, (2002) vol. 30, No. 2, pp. 605-613.
Hirano, et al., ATP-dependent aggregation of single-stranded DNA by a bacterial SMC homodimer,: Then EMBO Journal, (1998), vol. 17, No. 23, pp. 7139-7148.
Lee, "Ligase Chain Reaction," The International Association of Biological Stanodardization, (1996), No. 24, pp. 197-199.
Lee, et al., "DNA sequencing with dye-labled terminators and T7 DNA polymerase: effect of dyes and dNTPs on incorporation of dye-terminators and probability analysis of termination fragments," Nucleic Acids Research, (1992) vol. 20, No. 10, pp. 2471-2483.
Madiraju, et al., "Evidence for ATP Binding and Double-Stranded DNA Binding by *Escherichia coli* RecF Protein" Journal of Bacteriology, Dec. 1992, vol. 174, No. 23, jpp. 7705-7710.
Norais, et al., "DdrB Protein, an Alternative Deinococcus radiodurans SSB Induced by Ionizing Radiation," Journal of Biological Chemistry, Aug. 7, 2009, vol. 284, No. 32, pp. 21402-21412.
Palanichelvam, et al., "The capsid protein of tomato yellow leaf curl virus binds cooperatively to single-stranded DNA," Journal of General Virology, (1998) vol. 79, pp. 2829-2833.
Thorslund., et al., "The Breast cancer tumor suppressor BRCA2 promotes the specific targeting of RAD51 to single-stranded DNA," Nature Structural & Molecular Biology, Oct. 2010, vol. 17, No. 10, pp. 1263-1265.
Communication Pursued to Article 94(3) EPC dated May 23, 2018 in European Patent Application No. 14 706 709.4, 5 pages.
Lawyer, et al., "High-Level Expression, Purification, and Enzymatic Characterization of Full-Length Thermus aquaticus DNA Polymerase and a Truncated form Deficient in 5' to 3' Exonuclease Activity," Cold Spring Harbor Laboratory Press, (1993), vol. 2, pp. 275-287.
Washington, et al., "Human DNA Polymerase Utilitzes Different Nucleotide Incorporation Mechanisms Dependent upon the Template Base," Molecular and Cellular Biology, (2004) vol. 24, No. 2, pp. 936-943.
Haung, et al., Klenow Fragment Discriminates Against the Incorporation of the Hyperoxiized dGTP Lesion Spiroiminodihydantoin into DNA, Chem Res. Toxicol, (Dec. 21, 2015), vol. 28, No. 12, pp. 2325-2333.
Travaglini, et al., "Kinetic Analysis of *Escherichia coli* Deoxyribonucleic Acid Polymerase I*," The Journal of Biological Chemistry, (1975), vol. 250, No. 22, pp. 8647-8656.

U.S. Appl. No. 12/553,667, filed Sep. 3, 2009 by Xinsheng Ling, Non-Final Office action dated Dec. 31, 2013.
U.S. Appl. No. 12/243,451, filed Oct. 1, 2008 by John S. Oliver et al., issued as U.S. Pat. No. 8,278,047 on Oct. 2, 2012.
U.S. Appl. No. 11/538,189, filed Oct. 3, 2006 by Xinsheng Ling et al., Office action dated Mar. 20, 2013, and Final Office action dated Nov. 19, 2013.
U.S. Appl. No. 12/732,870, filed Mar. 26, 2010 by John S. Oliver et al., Final Office action dated April 10, 2013, and Non-Final Office action dated Nov. 13, 2013.
U.S. Appl. No. 12/732,259, filed Mar. 26, 2010 by Peter Goldstein et al., issued as U.S. Pat. No. 8,455,260 on Jun. 4, 2013.
U.S. Appl. No. 12/553,684, filed Sep. 3, 2009 by John S. Oliver, issued as U.S. Pat. No. 8,262,879 on Sep. 11, 2012.
U.S. Appl. No. 13/567,595, filed Aug. 6, 2012 by John S. Oliver, Office action dated Apr. 11, 2013, and Final Office action dated Jan. 6, 2014.
U.S. Appl. No. 12/789,817, filed May 28, 2012 by John S. Oliver et al., issued as U.S. Pat. No. 8,246,799 on Aug. 21, 2012.
U.S. Appl. No. 12/891,343, filed Sep. 27, 2011 by John S. Oliver, Non-Final Office action dated May 23, 2013, and Notice of Allowance dated Jan. 28, 2014.
U.S. Appl. No. 13/330,646, filed Dec. 19, 2011 by John S. Oliver et al., Non-Final Office action dated Jun. 27, 2013.
U.S. Appl. No. 12/732,870, filed Mar. 26, 2010 by John S. Oliver et al., Final Office action dated May 5, 2014.
U.S. Appl. No. 12/732,259, filed Mar. 26, 2010 by Peter Goldstein et al., Notice of Allowance dated Feb. 4, 2013.
U.S. Appl. No. 13/292,415, filed Nov. 9, 2011 by Peter Goldstein, Non-Final Office action dated Apr. 24, 2014.
U.S. Appl. No. 12/891,343, filed Sep. 27, 2011 by John S. Oliver, issued at U.S. Pat. No. 8,715,933 on May 6, 2014.
U.S. Appl. No. 13/589,608, filed Aug. 20, 2012 by John S. Oliver et al., Non-Final Office Action dated Dec. 11, 2014.
U.S. Appl. No. 13/589,608, filed Aug. 20, 2012 by John S. Oliver et al., Notice of Allowance dated Feb. 3, 2015.
U.S. Appl. No. 11/538,189, filed Oct. 3, 2006 by Xinsheng Ling et al., Final Office action dated Mar. 11, 2015.
U.S. Appl. No. 12/732,870, filed Mar. 26, 2010 by John S. Oliver et al., Examiner's Answer dated May 26, 2015.
U.S. Appl. No. 12/553,667, filed Sep. 3, 2009 by Xinsheng Ling, Notice of Allowance dated Jul. 16, 2014.
U.S. Appl. No. 13/567,595, filed Aug. 6, 2012 by John S. Oliver, Notice of Allowance dated Jun. 9, 2014.
U.S. Appl. No. 14/331,629, filed Jul. 15, 2014 by John S. Oliver.
U.S. Appl. No. 13/292,415, filed Nov. 9, 2011 by Peter Goldstein, Notice of Allowance dated Jun. 24, 2014.
U.S. Appl. No. 14/157,136, filed Jan. 16, 2014 by John S. Oliver et al., Non-Final Office action dated Sep. 30, 2015.
U.S. Appl. No. 14/036,509, filed Sep. 25, 2013 by John S. Oliver et al., Non-Final Office action dated Sep. 15, 2015.
U.S. Appl. No. 14/200,601, filed Mar. 7, 2014 by Stan Rose, Non-Final Office action dated Jan. 4, 2016.
U.S. Appl. No. 14/468,959, filed Aug. 26, 2014.
U.S. Appl. No. 14/852,086, filed Sep. 11, 2015 by Jeffrey H. Stokes et al.

* cited by examiner

SEQUENCE LISTING

<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cttctagatt ctag                                                           14

<210> SEQ ID NO 2
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cuucuagauu cuag                                                           14

ASSAY METHODS USING DNA BINDING PROTEINS

CROSS-REFERENCE TO RELATED APPLICATION

This application claims priority to and the benefit of U.S. Provisional Patent Application No. 61/441,945, filed Feb. 11, 2011, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Apr. 10, 2012, is named NAB008.txt and is 732 bytes in size.

FIELD OF INVENTION

The present invention relates generally to assay methods for the analysis of biopolymers. Mapping and sequencing of such biopolymers is contemplated herein.

BACKGROUND

A number of different approaches for sequencing nucleic acids exist. The traditional methods are the dideoxy-chain termination method described by Sanger et al., Proc Natl. Acad. Sci. USA, (1977) 74: 5463-67 and the chemical degradation method described by Maxam et al., Proc. Natl. Acad. Sci. USA, (1977) 74: 560-564. Of these two methods, the Sanger procedure has been the most widely used. The original Sanger method relied on radioactive labeling of the reaction products and separation of the reaction products by slab gel electrophoresis.

Both the Sanger and Maxam methods are time- and labor-intensive. The start of the Human Genome Project was the impetus for the development of improved, automated systems to perform Sanger sequencing. As a result, detection of fluorescence has replaced autoradiography and capillary electrophoresis has replaced the ultrathin slab gels originally used to separate reaction products. Automated sequencers have been developed and are capable of processing large numbers of samples without operator intervention.

The completion of the Human Genome Project has refocused the need for new technologies that are capable of rapidly and inexpensively determining the sequence of human and other genomes. There is has been much discussion in recent years about personalized medicine. The vision of personalized medicine involves each individual having his or her complete genome sequenced at high accuracy and using this information to guide clinical care, specifically for risk stratification of patients and pharmacogenomics.

In recent years, a number of technological advances have been developed enabling a great reduction in the cost of sequencing and substantially increasing the amount of sequence data produced. Most sequencing methods currently available utilize optical detection for the determination of the DNA sequence. The most prevalent sequencing methods are referred to as sequencing by synthesis (SBS).

Typical SBS methods involve the stepwise synthesis of a strand of DNA that is complementary to a template sequence from the target genome to be sequenced. The SBS methods can be divided into those that are performed in batch mode and those that are performed in real-time. The batch mode processes rely on the stepwise synthesis of the new DNA strand with the limitation that the synthesis is only allowed to proceed for one nucleotide position, for one nucleotide type, or for the combination of one nucleotide position and one nucleotide type. The incorporation of the nucleotide occurs in parallel for large numbers of templates. Detection is achieved using a variety of methods.

A batch mode SBS method utilizing a single nucleotide type is used by Roche for pyrosequencing with the 454 platform. The Roche technology (see, e.g., Margulies et al. (2005) Nature, 437:376-380; U.S. Pat. Nos. 6,274,320; 6,258,568; 6,210,891) utilizes pyrosequencing. The method depends on several enzymes and cofactors to produce luminescence when a nucleotide is incorporated. A single nucleotide species is introduced into a large number of small reaction vessels each containing multiple copies of a single template. The incorporation of the nucleotide is accompanied by light emission. When the reaction has run to completion, the reagents are washed from the reaction volumes and a next nucleotide and its required reagents are washed into the reactions. Each template is thus extended in an iterative fashion, one nucleotide at a time. Multiple incorporations of the same nucleotide require the quantitative determination of the amount of light emitted. Homopolymer tracts in templates may be difficult to accurately sequence as the incremental amount of light emitted for each subsequent position in the homopolymer becomes small compared to the total amount emitted.

In a second SBS method, platforms by Helicos (see, e.g., Quake et al Proc. Nat. Acad. Sci. USA (2003) 100: 3960-3964; U.S. Pat. Nos. 6,818,395; 6,911,345; 7,297,518; 7,462,449 and 7,501,245), Illumina (see, e.g., Bennett et al. Pharmacogenomics (2005) 6:373-382), and Intelligent Bio-Systems (see, e.g., Ju et al. Proc. Nat. Acad. Sci. USA (2006) 103:19635-19640) allow only the incorporation of a single nucleotide at each step. Template strands are attached to a solid support and a primer sequence is annealed. A polymerase is used to extend the primer to make a complement to the template. The nucleotides are derivatized such that after the incorporation of a single nucleotide, the growing strand is incapable of further extension. The nucleotides are further derivatized to make them fluorescent. In the Helicos technology, the four nucleotides are labeled with the same fluorescent tag. This requires that each nucleotide type be added separately. In contrast, the Illumina and Intelligent Bio-Systems technologies utilize four different fluorescent tags so that a mixture of all four derivatized nucleotides may be added at the same time. For both technologies, the incorporation of a nucleotide is accompanied by the appearance of fluorescence in the growing strand. In the case of Illumina, the wavelength of the fluorescence emission indicates the identity of the newly incorporated nucleotide. In the Helicos technology, only a single nucleotide type is added at each cycle. Thus, the appearance of fluorescence at a position on the solid support indicates the incorporation of the added nucleotide for that template. Templates that do not incorporate the nucleotide present in the reaction remain dark.

Following the observation of any incorporated fluorescence, the blocking groups and fluorescent tags are removed prior to the next cycle. Multiple cycles result in the acquisition of sequence data for many templates in a single run. The instrumentation typical for these technologies is said to allow for the automated acquisition of sequence information for hundreds of thousands to millions of templates in parallel.

SBS methods may also be performed in real-time. In real-time SBS, polymerase is used to incorporate fluorescently labeled nucleotides and the fluorescence is observed during DNA strand synthesis. The four nucleotides are labeled with different fluorescent tags. The fluorescent tags are attached to the terminal phosphate of the nucleotide triphosphate. During incorporation of the nucleotide into the growing strand the fluorophore is released to solution and the growing strand remains non-fluorescent. The identity of the incorporated strand is determined while the nucleotide resides in the active site of the enzyme and before the cleaved diphosphate is released to bulk solution.

The fluorescence of the incorporated nucleotide typically is measured in a background fluorescence from a much larger concentration of unincorporated nucleotide. Pacific Biosciences (see, e.g., U.S. Pat. Nos. 7,170,050; 7,302,146; 7,315,019; 7,476,503; and 7,476,504) identifies the incorporated nucleotide based on the residence time in the polymerase active site. Fluorescence emission from the active site for an appropriate time indicates incorporation and the emission wavelength determines the identity of the incorporated nucleotide. Polymerase is attached to the bottom of zero-mode waveguides. Zero-mode waveguides are reaction cells whose dimensions limit the passage of light from the excitation sources. Thus, only fluorescent tags close to the bottom surface of the reaction volume are excited.

Visigen identifies the incorporated nucleotide through Fluorescent Resonant Energy Transfer (FRET) between an acceptor in the polymerase active site and a fluorescent tag on the nucleotide (see, e.g., U.S. Pat. Nos. 7,211,414 and 7,329,492). Only nucleotides held in the active site of the polymerase show fluorescence. Incorporation is identified by the residence time of the fluorescence in the active site and the nucleotide identity is determined by the emission wavelength.

Other recently developed methods to sequence DNA rely on hybridization and ligation. Both the SOLiD and Complete Genomics technologies rely on the combination of hybridization and ligation. The SOLiD system (Life Technologies) immobilizes short template strands via an adapter. A primer and a pool of labeled oligonucleotides containing two fixed positions and six degenerate positions is hybridized to the template. The primer hybridizes to the adaptor. Each pool consists of 16,384 different sequences. Four fluorescent dyes are used to label the oligonucleotides in a pool in a fashion that creates four subsets from the sixteen combinations at the two fixed positions. Thus, each fluorescent tag is associated with four of the sixteen possible combinations. Following hybridization, a ligase is added and any probes in the pool that hybridized contiguously with the primer are ligated to the primer. The fluorescence of the hybridized and ligated product is determined. The fluorescence defines which subset of sequences hybridized to the template and ligated to the primer. The terminal three bases and the associated fluorescent tag are cleaved from the hybridized and ligated oligonucleotide. Subsequent rounds of another round of hybridization, ligation, and cleavage are performed. In this first series of reactions, each cycle identifies a subset for the pair of nucleotides in the template that is 5 nucleotides downstream from subset of pairs that were identified in the last cycle. After several cycles, the primer, and the oligonucleotides that have been ligated to it, is washed off the template.

The entire procedure is repeated starting with a primer that is one nucleotide shorter than the original primer, then with primers that are two, three, and four nucleotides shorter than the original primer. These subsequent rounds shift the frame of interrogation so that the bases that make-up the template strand can be identified from the union between the two subsets of reaction that overlapped at that position.

Complete Genomics technology utilizes a similar hybridization and ligation method (see, e.g., US Patent Application Publication Nos. 20080234136; 20090005252; 20090011943; and 20090176652). In the Complete Genomics technology, a primer is hybridized to an adaptor that is attached to the end of the template. A series of pools of oligonucleotides is constructed. In each pool, the nucleotide at a single position is identified by using four-color fluorescence. The remaining positions are degenerate. The first pool is hybridized to the template. Oligonucleotides that hybridize adjacent to the primer are subsequently ligated. After washing excess oligonucleotides away, the fluorescence of the ligated oligonucleotide identifies the nucleotide at the defined position in that pool. The ligated primer and oligonucleotide are washed off the template and the process is repeated with the next pool of oligonucleotides that probe the next position down from the primer.

The SBS and hybridization-ligation methods generate short pieces or reads of DNA sequence. While the short reads can be used to re-sequence human genomes, they are not favorable for the de novo assembly of human genomes. With the recent realization that human genomes contain large numbers of inversions, translocations, duplications, and indels (e.g., mutations that include both insertions, deletions, and the combination thereof), the quality of human genome data from short reads is even more suspect. Genetic rearrangements are even more prevalent in cancer.

While variations of the short read technologies that incorporate paired-end reads have been proposed and the length of the sequence data from these technologies has increased incrementally over the last two years, it is clear that longer read technologies are necessary for the accurate assembly of human genome data.

In addition to the undesirable nature of short reads, all of the DNA sequencing methods described above employ optical detection. The throughput of optical methods limits the ultimate performance characteristics of any of these sequencing technologies. Optical methods are capable of identifying single molecules. However, the time required to observe and accurately identify events is typically too slow to meet the need for higher throughput. While the current generation of sequencing technologies has lowered the cost of sequencing by orders of magnitude in comparison to the methods used to sequence the first human genomes, the methods remain too slow, costly, and inaccurate for routine analysis of human genomes.

A need therefore exists for efficient methods and devices capable of rapid and accurate nucleic acid sequencing for de novo assembly of human genomes. It is desirable to have long read lengths and to use as little nucleic acid template as possible. Moreover, single-molecule optical detection of DNA has limitations with respect to sensitivity and speed.

Thus, there remains a need for improved methods and devices for the analysis of biopolymers, including methods and devices for mapping and sequencing such biopolymers.

SUMMARY

Embodiments of the invention provide assay methods for preparing analyte samples for mapping and sequencing using nanopore, micro-channel or nano-channel analysis devices.

In an aspect, an embodiment of the invention includes a method for preparing a biomolecule analyte. The method includes: a) providing a single-stranded DNA or RNA template; b) hybridizing a first plurality of identical, sequence specific oligonucleotide probes to the template, each probe having a 5' end and a 3' end, to thereby form an analyte having at least one single-stranded region and at least two duplex regions; c) conducting a base extension reaction in the at least one single-stranded region from the 3' end of a hybridized probe toward the 5' end of an adjacent hybridized probe; d) terminating the base-extension reaction such that there remains for each single-stranded region a single-stranded portion thereof adjacent to the 5' end of each hybridized probe, and e) reacting the resulting analyte with a binding moiety that selectively binds to the at least one single-stranded portion to thereby prepare the biomolecule analyte.

One or more of the following features may be included. The probes may include single-stranded DNA and/or RNA. The base extension reaction may be performed by a DNA or RNA polymerase. The binding moiety may include a protein, such as RecA, T4 gene 32 protein, f1 geneV protein, human replication protein A, Pf3 single-stranded binding protein, adenovirus DNA binding protein, and/or *E. coli* single-stranded binding protein. A length of each probe may be selected from a range of 4 to 12 bases.

Steps a-e may be performed sequentially. Steps a-e may be repeated sequentially by replacing the first plurality of probes with a subsequent plurality of different unique probes. At least a portion of the probes in the first plurality of probes has attached thereto a detectable tag.

The biomolecule analyte may be configured for detection of positional information in a nanopore system. Changes in an electrical property across a nanopore may be monitored as the biomolecule analyte is translocated therethrough, the changes in the electrical property being indicative of regions including or lacking the binding moiety. Regions of the biomolecule analyte including or lacking the binding moiety may be differentiated based, at least in part, on the changes in the electrical property, to thereby determine binding moiety locations.

The biomolecule analyte may be configured for detection of positional information in a fluidic channel system. The fluidic channel system may include a micro-channel or a nano-channel. Changes in an electrical property across a fluidic channel may be monitored as the biomolecule analyte is translocated therethrough, the changes in the electrical property being indicative of regions including or lacking the binding moiety. Regions of the biomolecule analyte including or lacking the binding moiety may be differentiated based, at least in part, on the changes in the electrical property, to thereby determine binding moiety locations.

A sequence of at least a portion of the single-stranded DNA or RNA template may be determined according to the determined binding moiety locations.

Sequence-specific oligonucleotide analog probes such as LNAs, PNAs or 2'-methoxy nucleotide analogs may be substituted for the sequence specific oligonucleotide probes. The first plurality of identical, sequence specific oligonucleotide probes may be replaced by a pool of sequence specific oligonucleotide probes including at least a first plurality of identical, sequence specific oligonucleotide probes and a second plurality of identical, sequence specific oligonucleotide probes, with the probes of the second plurality being different from the probes of the first plurality.

In another aspect, embodiments of the invention includes a method for preparing a biomolecule analyte by: a) providing a single-stranded DNA template; b) hybridizing a first plurality of identical, sequence specific RNA probes to the template, each probe having a 5' end and a 3' end, to thereby form an analyte having at least one single-stranded region and at least one duplex region; c) conducting a base extension reaction in the at least one single-stranded region from the 3' end of a hybridized probe; d) allowing the base-extension reaction to fill each single-stranded region on the analyte; e) removing the RNA probes to provide the analyte with at least one single-stranded segment in the region to which an RNA probe had been hybridized; and f) reacting the resulting analyte with a binding moiety that selectively binds to the single-stranded segment, to thereby prepare the biomolecule analyte.

One or more of the following features may be included. The base extension reaction may be performed by a DNA or RNA polymerase. The binding moiety may include a protein, such as RecA, T4 gene 32 protein, f1 geneV protein, human replication protein A, Pf3 single-stranded binding protein, adenovirus DNA binding protein, and/or *E. coli* single-stranded binding protein. A length of each probe may be selected from a range of 4 to 12 bases.

Steps a-f may be performed sequentially. Steps a-f may be repeated sequentially by replacing the first plurality of probes with a subsequent plurality of different unique probes.

The RNA probes may be removed by reacting the analyte with hydroxyl ions.

The biomolecule analyte may be configured for detection of positional information in a nanopore system. Changes in an electrical property across a nanopore may be monitored as the biomolecule analyte is translocated therethrough, the changes in the electrical property being indicative of regions including or lacking the binding moiety. Regions of the biomolecule analyte including or lacking the binding moiety may be differentiated based, at least in part, on the changes in the electrical property, to thereby determine binding moiety locations.

The biomolecule analyte may be configured for detection of positional information in a fluidic channel system. The fluidic channel system may include a micro-channel or a nano-channel. Changes in an electrical property across a fluidic channel may be monitored as the biomolecule analyte is translocated therethrough, the changes in the electrical property being indicative of regions including or lacking the binding moiety. Regions of the biomolecule analyte including or lacking the binding moiety may be differentiated based, at least in part, on the changes in the electrical property, to thereby determine binding moiety locations.

A sequence of at least a portion of the single-stranded DNA or RNA template may be determined according to the determined binding moiety locations.

The first plurality of identical, sequence specific RNA probes may be replaced by a pool of sequence specific RNA probes including at least a first plurality of identical, sequence specific RNA probes and a second plurality of identical, sequence specific RNA probes, the probes of the second plurality being different from the probes of the first plurality.

In yet another aspect, embodiments of the invention include a method for preparing a biomolecule analyte. The method includes: a) providing a single-stranded DNA or RNA template; b) hybridizing a first plurality of identical, sequence specific oligonucleotide probes to the template, to thereby form an analyte having at least one single-stranded region and at least one duplex region; and c) reacting the resulting analyte with a binding moiety that selectively binds to the at least one duplex region to thereby prepare the biomolecule analyte.

One or more of the following features may be included. The probes may include single-stranded DNA and/or RNA. The binding moiety may include a protein, such as RecA, T4 gene 32 protein, f1 geneV protein, human replication protein A, Pf3 single-stranded binding protein, adenovirus DNA binding protein, and/or *E. coli* single-stranded binding protein. A length of each probe may be selected from a range of 4 to 12 bases.

Steps a-c may be performed sequentially. Steps a-c may be repeated sequentially by replacing the first plurality of probes with a subsequent plurality of different unique probes. At least a portion of the probes in the first plurality of probes has attached thereto a detectable tag.

The biomolecule analyte may be configured for detection of positional information in a nanopore system. Changes in an electrical property across a nanopore may be monitored as the biomolecule analyte is translocated therethrough, the changes in the electrical property being indicative of regions including or lacking the binding moiety. Regions of the biomolecule analyte including or lacking the binding moiety may be differentiated based, at least in part, on the changes in the electrical property, to thereby determine binding moiety locations.

The biomolecule analyte may be configured for detection of positional information in a fluidic channel system. The fluidic channel system may include a micro-channel or a nano-channel. Changes in an electrical property across a fluidic channel may be monitored as the biomolecule analyte is translocated therethrough, the changes in the electrical property being indicative of regions including or lacking the binding moiety. Regions of the biomolecule analyte including or lacking the binding moiety may be differentiated based, at least in part, on the changes in the electrical property, to thereby determine binding moiety locations.

A sequence of at least a portion of the single-stranded DNA or RNA template may be determined according to the determined binding moiety locations.

Sequence specific oligonucleotide analog probes, such as LNAs, PNAs and 2'-methoxy nucleotide analogs, may be substituted for the sequence specific oligonucleotide probes. The first plurality of identical, sequence specific oligonucleotide probes may be replaced by a pool of sequence specific oligonucleotide probes including at least a first plurality of identical, sequence specific oligonucleotide probes and a second plurality of identical, sequence specific oligonucleotide probes, the probes of the second plurality being different from the probes of the first plurality.

In another aspect, embodiments of the invention include a method for preparing a biomolecule analyte. The method includes: a) providing a single-stranded DNA or RNA template; b) hybridizing a first plurality of identical, sequence specific oligonucleotide probes to the template, to thereby form an analyte having at least one single-stranded region and at least one duplex region; and c) reacting the resulting analyte with a binding moiety that selectively binds to the at least one single-stranded region, to thereby prepare the biomolecule analyte.

One or more of the following features may be included. The probes may include single-stranded DNA and/or RNA. The binding moiety may include a protein, such as RecA, T4 gene 32 protein, f1 geneV protein, human replication protein A, Pf3 single-stranded binding protein, adenovirus DNA binding protein, and/or *E. coli* single-stranded binding protein. A length of each probe may be selected from a range of 4 to 12 bases.

Steps a-c may be performed sequentially. Steps a-c may be repeated sequentially by replacing the first plurality of probes with a subsequent plurality of different unique probes. At least a portion of the probes in the first plurality of probes has attached thereto a detectable tag.

The biomolecule analyte may be configured for detection of positional information in a nanopore system. Changes in an electrical property across a nanopore may be monitored as the biomolecule analyte is translocated therethrough, the changes in the electrical property being indicative of regions including or lacking the binding moiety. Regions of the biomolecule analyte including or lacking the binding moiety may be differentiated based, at least in part, on the changes in the electrical property, to thereby determine binding moiety locations.

The biomolecule analyte may be configured for detection of positional information in a fluidic channel system. The fluidic channel system may include a micro-channel or a nano-channel. Changes in an electrical property across a fluidic channel may be monitored as the biomolecule analyte is translocated therethrough, the changes in the electrical property being indicative of regions including or lacking the binding moiety. Regions of the biomolecule analyte including or lacking the binding moiety may be differentiated based, at least in part, on the changes in the electrical property, to thereby determine binding moiety locations.

A sequence of at least a portion of the single-stranded DNA or RNA template may be determined according to the determined binding moiety locations.

Sequence specific oligonucleotide analog probes such as LNAs, PNAs and 2'-methoxy nucleotide analogs may be substituted for the sequence specific oligonucleotide probes. The first plurality of identical, sequence specific oligonucleotide probes may be replaced by a pool of sequence specific oligonucleotide probes including at least a first plurality of identical, sequence specific oligonucleotide probes and a second plurality of identical, sequence specific oligonucleotide probes, the probes of the second plurality being different from the probes of the first plurality.

In some embodiments, the probes are single-stranded DNA or RNA, and they may optionally be provided with tags that enhance detection in analysis devices. Based on the nature of the tags, the binding moiety may bind to the tags as well as to regions of the analyte, further enhancing detection. Alternatively, the probes may include oligonucleotide analogs such as Locked Nucleic Acids (LNAs), Peptide Nucleic Acids (PNA s) or 2'-methoxy nucleotide analogs. Base extension reactions are performed using DNA polymerase or RNA polymerase, as appropriate.

In any of the above-described embodiments, one or more of the features described in this paragraph and in the paragraphs that follow may be included. The process steps may be repeated using subsequent pluralities of matching probes having a known binding selectivity different from the known binding selectivity of the first plurality of probes. The first plurality of probes may be hybridizing oligonucleotides having n number of bases, with n preferably ranging from 4 to 12. Each process may be repeated sequentially by replacing the first plurality of probes with a subsequent plurality of each of the different unique probes within the entire library of $4^n$ n-mer probes. A portion of the library of $4^n$ n-mer probes may be used, such as about 85%, 75%, 65%, 55%, 45%, or 33% of the library. The sequential repetition of the process may be conducted in a linear or parallel series of reactions.

Alternatively, rather than employing a single plurality of identical, sequence specific oligonucleotide probes, a pool of probes comprising a first plurality of identical, sequence specific oligonucleotide probes and a second plurality of identical, sequence specific oligonucleotide probes, different from the first plurality, may be employed.

The biomolecule to be analyzed may be DNA or RNA. The binding moiety may be a protein. Examples of suitable proteins include RecA, T4 gene 32 protein, f1 geneV protein, human replication protein A, Pf3 single-stranded binding protein, adenovirus DNA binding protein, and E. coli single-stranded binding protein.

The products of the assay methods described herein may be analyzed in an apparatus using a nanopore or a fluidic channel such as a micro-channel or nano-channel to detect probes or probe positions on the biomolecule being analyzed. Suitable apparatus are described, for example, in U.S. patent application Ser. No. 12/789,817, published as U.S. Publication No. 2010/0310421, incorporated herein by reference in its entirety Such systems use electrical detection methods to determine the presence and/or the relative position of the oligonucleotide probes. The products of the assay methods described herein may be sequenced in accordance with sequencing methods such as those described in U.S. patent application Ser. No. 13/292,415, incorporated herein by reference in its entirety.

An electrical property across a nanopore or fluidic channel as the analyte translocates therethrough may be monitored, with changes in the electrical property being indicative of regions on the analyte including or lacking the binding moiety. Furthermore, differentiating between regions on the analyte including or lacking the binding moiety, allows a determination of binding moiety locations on the analyte.

DETAILED DESCRIPTION

Figure 1:
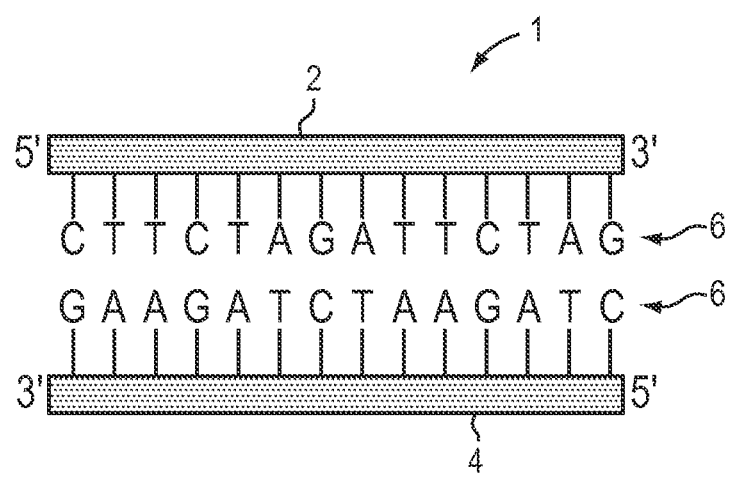
FIG. 1 is a schematic depiction of a DNA molecule (SEQ ID NO: 1).

As used in this description and the accompanying claims, the following terms shall have the meanings given, unless the context indicates otherwise:

A "biomolecule analyte" or "target analyte" means a biomolecule, for example, having sequence information that is to be determined using embodiments of the present invention. The target may be a biomolecule such as, for example, deoxyribonucleic acid, a ribonucleic acid, a protein, or a polypeptide. The target may be single-stranded or double-stranded.

A "probe" means any molecule or assembly of molecules capable of sequence-specific covalent or non-covalent binding to an analyte.

A "tag" means a moiety that is attached to a probe in order to make the probe more visible to a detector. These tags may be, for example, proteins, double-stranded DNA, single-stranded DNA or other molecules. Exemplary tags that will bind RecA include single-stranded or double-stranded DNA. Another useful tag may be a dendrimer, for example. Optionally, tags have either a larger volume than the probe or a different charge so that they slow translocation of the biomolecule through a nanopore, or through a nano-channel or micro-channel.

Disclosed herein are methods that increase the signal-to-noise ratio in translocation detection of biomolecules that have been hybridized to probes. In one embodiment, a single-stranded biomolecule may be hybridized with a probe. The hybridized biomolecule may then be incubated with a protein or enzyme that binds to the biomolecule and forms at least a partial coating along the biomolecule.

Coated biomolecules typically have greater uniformity in their translocation rates, which leads to a decrease in positional error and thus more accurate sequencing. Due to its increased diameter, a coated biomolecule generally translocates through a sequencing system at a slower speed than a non-coated biomolecule. The translocation is preferably slow enough so that a signal can be detected during its passage from a first chamber into a second chamber. The translocation rate or frequency may be regulated by introducing a salt gradient between the chambers. Exemplary salt concentration ratios of the cis to the trans side of the chamber may include, but are not limited to, 1:2, 1:4, 1:6, and 1:8. For example, salt concentrations may range from about 0.5 M KCl to about 1 M KCl on the cis side and from about 1 M KCl to about 4 M KCl on the trans side. The signal is preferably strong enough to be detected using known methods or methods described herein. Exemplary signal-to-noise ratios include, but are not limited to, 2:1, 5:1, 10:1, 15:1, 20:1, 50:1, 100:1, and 200:1. With a higher signal-to-noise ratio, a lower voltage may be used to effect translocation.

In one embodiment, a biomolecule of interest is hybridized with the entire library of probes of a given length. For example, the biomolecule of interest can be hybridized with the entire universe of 4096 (i.e., $4^6$) possible six-mers. The hybridization can be done sequentially (i.e., one probe after another) or in parallel (i.e., a plurality of biomolecules of interest are each separately hybridized simultaneously with each of the possible probes.) Alternatively, the probes can be separated from each other in both space and time. Additionally, more than one probe type may be hybridized to the same biomolecule of interest at the same time.

The set of probes used to perform the sequencing may be a subset of the complete library of probes of a given length, such as about 85%, 75%, 65%, 55%, 45%, or 33% of the library. For instance, if sequencing is performed on a biomolecule that starts as double-stranded DNA, then only one-half of the probes that make up a library may be needed. Other subsets of the library may be designed to allow sequencing as well. If some information concerning the target sequence is known prior to performing the sequencing reaction, it may be possible to use a small subset of the total library. For instance, if the sequencing reaction is being performed to determine if single nucleotide polymorphisms are present with respect to a reference sequence, then a small number of probes with respect to the complete library may be used. Alternatively, the set of probes may not all be the same length. In an embodiment, a set of at least two probes may be used for hybridization, rather than an entire library of probes or subset thereof. In another embodiment, probes may be separated by (GC) content or other determinants of probe binding strength, in order to allow for optimization of reaction conditions. By separating the probes based on relative properties, multiple probes may be incorporated into a single hybridization reaction. Further, the probes may be grouped based on their related optimum reaction environment preferences. In yet another embodiment, pools of probes may be simultaneously hybridized to a biomolecule of interest. A pool of probes is a group of probes of different composition, each of which may likely be present in many copies. The composition of the probes may be chosen so as to reduce the chance of competitive binding to the biomolecule of interest. Alternatively, the composition of multiple pools may be chosen so that the same competitive binding is not present in all pools occupied by a single probe.

In still another embodiment, the probes may be attached to tags, making electrical fluctuations more noticeable as the hybridized probes translocate through the sequencing system. In addition, different tags may be used to help distinguish among the different probes. These tags may be proteins, double-stranded DNA, single-stranded DNA or other molecules.

It should be understood that the invention is not intended to be limited strictly to DNA and RNA oligonucleotide probes. Rather, it is envisioned that oligonucleotide analog probes such as those comprising LNAs, PNAs and 2'-methoxy nucleotide analogs may be used as well.

In embodiments of the present invention, the biomolecule may be hybridized with sequence-specific probes prior to being reacted with a binding moiety such as a protein. The probes may or may not have tags attached to them. If the probe has an attached tag composed of single- or double-stranded DNA, the binding moiety, such as the protein RecA, may coat (i) the single-stranded target, (ii) the double-stranded regions where hybridization between the single-stranded target and (iii) the probe has occurred, and the tag attached to the probe. Alternatively, the bound probes and associated tags may have a different affinity for the binding moiety than for the biomolecule. If the tags have an essentially equal affinity for the binding moiety, then both the tag and the target may be coated. If the tag or probe has a greater affinity for the binding moiety, selective coating may be achieved. If the tag or probe has a lower affinity for the binding moiety, it may selectively coat regions of the biomolecule that do not have probe bound. Since any region with bound protein will have a larger signal, differentiation of the hybridized and non-hybridized regions allows for greater accuracy in determining the position of hybridization.

The translocation of biomolecule/protein complexes through a nanopore, a nano-channel or a micro-channel sequencing system may include detecting an electrical signal indicative of the passage of coated regions. In one embodiment, the signal detected may be formed by passage of the tagged region of the biomolecule through the sequencing system. The time for translocation may be indicative of the length of the biomolecule. The detection step may discriminate between coated, uncoated, or multiply coated regions, as a coated region may have a signal about ten times that of an uncoated region. Increased signal-to-noise may increase confidence for the detection of the probes. Positional information of probe binding to target biomolecule allows for the mapping or sequencing of the biomolecule analyte.

Figure 2:
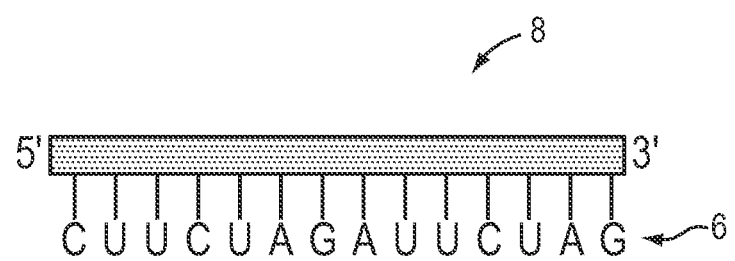
FIG. 2 is a schematic depiction of an RNA molecule (SEQ ID NO: 2).

In one embodiment, the process of sequencing a biomolecule such as single-strands of DNA or RNA using one or more probes may performed as follows. Suitable processes are also described in U.S. Ser. No. 11/538,189, published as U.S. Publication No. 2007/0190542, incorporated herein by reference in its entirety. Referring to FIG. 1, a DNA molecule 1 is schematically depicted and is structured in two strands 2, 4 positioned in anti-parallel relation to one another. Each of the two opposing strands 2, 4 may be sequentially formed from repeating groups of nucleotides 6 where each nucleotide 6 consists of a phosphate group, 2-deoxyribose sugar and one of four nitrogen-containing bases. The nitrogen-containing bases include cytosine (C), adenine (A), guanine (G) and thymine (T). DNA strands 2, 4 are read in a particular direction, from the top (called the 5' or "five prime" end) to the bottom (called the 3' or "three prime" end). Similarly, RNA molecules 8, as schematically depicted in FIG. 2, are polynucleotide chains, which differ from those of DNA 1 by having ribose sugar instead of deoxyribose and uracil bases (U) instead of thymine bases (T).

Traditionally, in determining the particular arrangement of the bases 6 and thereby the sequences of the molecules, a process called hybridization may be utilized. The hybridization process is the coming together, or binding, of two genetic sequences with one another. This process is predictable because the bases 6 in the molecules do not share an equal affinity for one another. T (or U) bases favor binding with A bases while C bases favor binding with G bases. Binding is mediated via hydrogen bonds that exist between the opposing base pairs. For example, A binds to T (or U) using two hydrogen bonds, while C binds to G using three hydrogen bonds.

Figure 3:
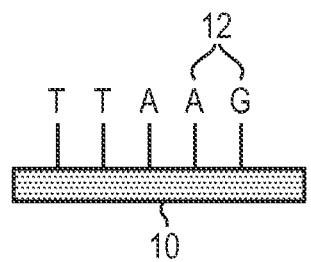
FIG. 3 is a schematic depiction of a hybridizing oligonucleotide probe.

A hybridizing oligonucleotide, i.e., a probe, may be used to determine and identify the sequence of bases in the molecule of interest. FIG. 3 illustrates a probe 10 that is a short DNA sequence having a known composition. Probes 10 may be of any length depending on the number of bases 12 that they include. For example, a probe 10 that includes six bases 12 is referred to as a six-mer probe wherein each of the six bases 12 in the probe 10 may be any one of the known four natural base types A, T(U), C or G. Alternately, the probe may include non-natural bases.

In this regard, the total number of unique probes 10 in a library is dependent upon the number of bases 12 contained within each probe 10 and the number of different types of bases in the probes. If only the four natural bases are used in probe 10, the total number of probes in the library is determined by the formula $4^n$ (four raised to the n power) where n is equal to the total number of bases 12 in each probe 10. Formulas for other arrangements or types of bases are well known in the art. Accordingly, the size of the probe library can be expressed as $4^n$ n-mer probes 10. For the purpose of illustration, in the context of a six-mer probe, the total number of possible unique, identifiable probe combinations includes $4^6$ (four raised to the sixth power) or 4096 unique six-mer probes 10. The inclusion of non-natural bases allows for the creation of probes that have spaces or wildcards therein in a manner that expands the versatility of the library, while reducing the number of probes that may be needed to reach the final sequence result. Probes that include universal bases organized into patterns with natural bases may also be used, for example those described in U.S. Pat. Nos. 7,071,324, 7,034,143, and 6,689,563, incorporated herein by reference in their entireties.

Figure 4:
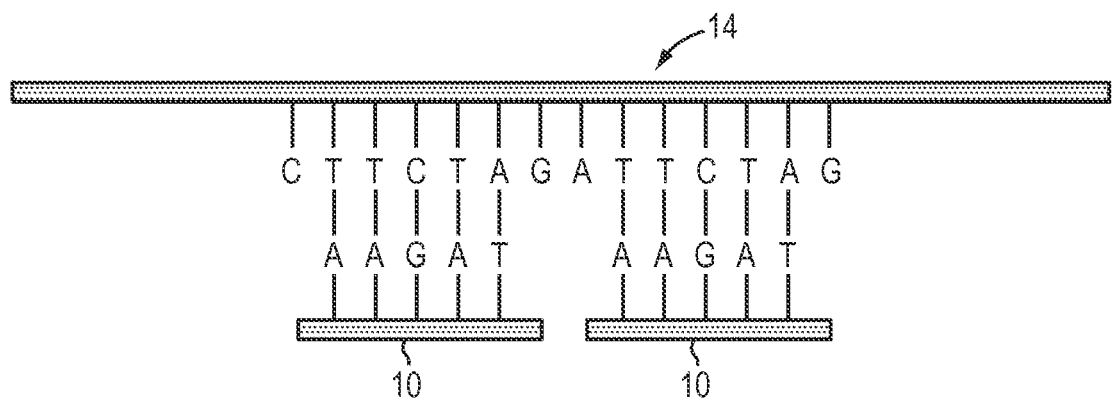
FIG. 4 is a schematic depiction of a single-stranded DNA molecule (SEQ ID NO: 1) hybridized with two identical probes.

The process of hybridization using probes 10, as depicted in FIG. 4, may begin by denaturing a double-stranded biomolecule, or by starting with a single-stranded biomolecule. Denaturing is accomplished usually through the application of heat or chemicals, such that the hydrogen bonds between adjacent portions of the biomolecule are broken. For example, the hydrogen bonds between the two halves of an original double-stranded DNA may be broken, leaving two single strands of DNA whose bases are now available for hydrogen bonding. After the biomolecule 14 has been denatured, a single-stranded probe 10 may be introduced to the biomolecule 14 to locate portions of the biomolecule 14 that have a base sequence that correlates to the sequence that is found in the probe 10. In order to hybridize the biomolecule 14 with the probe 10, the denatured biomolecule 14 and a plurality of the probes 10 having a known sequence are both introduced into a solution. The solution may be an ionic solution, such as a salt-containing solution. The mixture may be mixed to facilitate binding of the probes 10 to the biomolecule 14 strand along portions thereof that have a matched complementary sequence. Hybridization of the biomolecule 14 using the probe 10 may be accomplished before the biomolecule 14 is introduced into a nanopore sequencing apparatus or after the denatured biomolecule 14 has been placed into the cis chamber of such an apparatus. In this case, after the denatured biomolecule has been added to the cis chamber, buffer solution containing probes 10 with a known sequence is also added to the cis chamber and allowed to hybridize with the biomolecule 14 before the hybridized biomolecule is translocated.

Figure 5A:
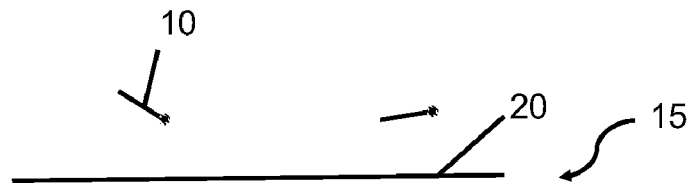
FIGS. 5(a)-5(d) are a schematic depiction of an assay method in accordance with an embodiment of the invention in which single-stranded DNA ("ssDNA") probes are bound to a single-stranded DNA or RNA analyte, a base extension reaction is carried out, and a binding moiety which binds to single-stranded portions of the resulting analyte is employed.

Embodiments of the present invention relate to improved methods for the preparation of biomolecule strands for analysis. In one embodiment, shown in FIGS. 5(a)-5(d), a denatured biomolecule analyte 15 is formed from a single-stranded DNA (ssDNA) or RNA fragment 20 exposed to ssDNA probes 10. As stated above, each probe 10 is a short ssDNA sequence of a known sequence. The probes 10 may be of any length depending on the number of bases that they include. As before, each of the probes is preferably of an identical sequence, thereby causing the probes to selectively hybridize only to portions of the biomolecule fragment 20 that have a complementary sequence. The fragment 20 and probes 10 are depicted prior to hybridization in FIG. 5(a). For purposes of clarity in FIGS. 5-12, probes 10 are shown having a small dot at the 3' end. This dot is not intended to signify a physical structure; rather, it is included in the Figures simply to designate the 3' end of the probe.

Figure 5B:
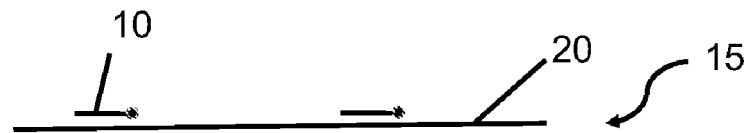

The biomolecule analyte 15 is shown in FIG. 5(b) following hybridization of the probes 10 to the biomolecule fragment 20. The resulting structure is a biomolecule fragment having, where hybridization has occurred, double-stranded, i.e., duplex, domains. The duplex domains are of a length corresponding to the length of the probes. Thus, in a case where a 6-mer probe is employed, the analyte 10 will comprise a single-stranded biomolecule fragment having a plurality of 6-mer duplex regions, formed by the hybridized probes.

Figure 5C:
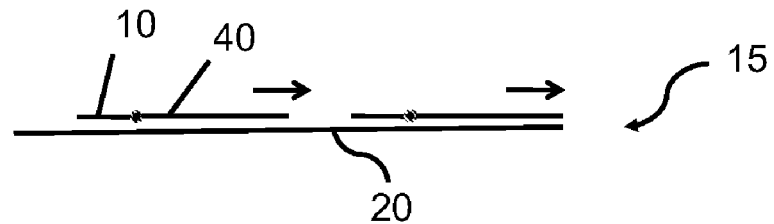

Following the hybridizing step, a base extension reaction, such as a primer extension reaction, utilizing for example, a polymerase and one or more nucleotides, is performed as depicted in FIG. 5(c). In such reactions, which form a nucleic acid complementary to a nucleic acid template, a primer complementary to a single-stranded DNA template is typically employed. Starting at the primer, a DNA polymerase may be used to add mononucleotides complementary to the template at the 3' end of the primer. Various base extension reactions will be familiar to those of ordinary skill in the art. Note that if the template includes RNA, an RNA dependent DNA polymerase is employed. Specifically, the hybridized probes 10 are extended from their 3' ends along the biomolecule fragment 20 to create duplex regions 40 on the analyte in gaps that had previously existed between the probe locations. Note, however, that the base extension reaction is intended to be limited in scope. Rather than extending from the 3' end of each probe to the 5' end of an adjacent probe, the base extension reaction may be terminated such that single-stranded segments remain on the biomolecule analyte 15 before the 5' end of each probe 10. The resulting analyte 15 structures, like those of FIG. 5(b), comprise duplex regions alternating with single-stranded regions. However, unlike the structures of FIG. 5(b) that may have relatively large single-stranded gaps between the bound probes 10, the resulting structures are characterized as being primarily duplexes with small single-stranded gaps.

Figure 5D:
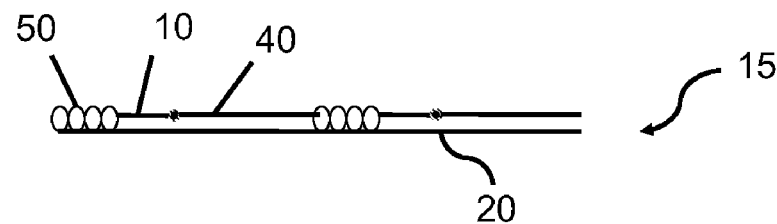

Finally, as depicted in FIG. 5(d), a binding moiety 50 which is selective to the single-stranded regions, (i.e., a protein such as *E. coli* single-stranded DNA binding protein), is reacted with the biomolecule analyte 15 in a manner such that the binding moiety fills the single-stranded gaps in the analyte.

The protein RecA from *E. coli* typically binds single- or double-stranded DNA in a cooperative fashion to form filaments containing the DNA in a core and an external sheath of protein (McEntee, K.; Weinstock, G. M.; Lehman, I. R. Binding of the RecA Protein of *Escherichia coli* to Single- and Double-Stranded DNA. *J. Biol. Chem.* 1981, 256, 8835, incorporated herein by reference in its entirety). DNA has a diameter of about 2 nm, while DNA coated with RecA has a diameter of about 10 nm. The persistence length of the DNA increases to around 950 nm, in contrast to 0.75 nm for single-stranded DNA or 50 nm for double-stranded DNA. T4 gene 32 protein is known to cooperatively bind single-stranded DNA (Alberts, B. M.; Frey, L. T4 Bacteriophage Gene32: A Structural Protein in the Replication and Recombination of DNA. *Nature,* 1970, 227, 1313-1318, incorporated herein by reference in its entirety). *E. coli* single-stranded binding protein binds single-stranded DNA in several forms depending on salt and magnesium concentrations (Lohman, T. M.; Ferrari, M. E. *Escherichia Coli* Single-Stranded DNA-Binding Protein: Multiple DNA-Binding Modes and Cooperativities. *Ann. Rev. Biochem.* 1994, 63, 527-570, incorporated herein by reference in its entirety). The *E. coli* single-stranded binding protein may form a varied coating on the biomolecule. The fl geneV protein is known to coat single-stranded DNA (Terwilliger, T.C. Gene V Protein Dimerization and Cooperativity of Binding of poly(dA). *Biochemistry* 1996, 35, 16652, incorporated herein by reference in its entirety), as is human replication protein A (Kim, C.; Snyder, R. O.; Wold, M. S. Binding properties of replication protein A from human and yeast cells. *Mol. Cell Biol.* 1992, 12, 3050, incorporated herein by reference in its entirety), Pf3 single-stranded binding protein (Powell, M. D.; Gray, D. M. Characterization of the Pf3 single-strand DNA binding protein by circular dichroism spectroscopy. *Biochemistry* 1993, 32, 12538, incorporated herein by reference in its entirety), and adenovirus DNA binding protein (Tucker, P. A.; Tsernoglou, D.; Tucker, A. D.; Coenjaerts, F. E. J.; Leenders, H.; Vliet, P. C. Crystal structure of the adenovirus DNA binding protein reveals a hook-on model for cooperative DNA binding. *EMBO J.* 1994, 13, 2994, incorporated herein by reference in its entirety). The protein-coated DNA may then be translocated through a nanopore as has been demonstrated with RecA bound to double-stranded DNA (Smeets, R. M. M.; Kowalczyk, S. W.; Hall, A. R.; Dekker, N. H.; Dekker, C. Translocation of RecA-Coated Double-Stranded DNA through Solid-State Nanopores. *Nano Lett.* 2009, incorporated herein by reference). Translocation of protein bound to single-stranded DNA is contemplated. The protein coating functions in the same manner for single-stranded DNA and double-stranded DNA.

It is important that the binding moiety 50 be distinguishable from duplex regions when the analyte is introduced to a nanopore or micro- or nanochannel sequencing system. As such, the locations of the binding moiety 50 on each fragment may be identified, leading to the location of each probe, since the binding moiety will end adjacent to the 5' end of each probe. Since the positions of the probes may then be readily determined, and as the analyte portions containing the probes will have regions complementary to the known probe sequences, one may determine the sequence and location of specific domains on the analyte. Numerous maps may be created, corresponding to the positions of different probes. The resulting maps may be combined and utilized to determine broader sequence information for the analyte.

A similar embodiment is depicted in FIGS. 6(a)-6(d). The analyte 60 is formed from a single-stranded DNA (ssDNA) or RNA fragment 20 exposed to tagged oligonucleotide probes 70. As stated above, each tagged probe 70 may include a short segment of ssDNA 10 of a known sequence. The probing segments 10 may be of any length depending on the number of bases that they include. As before, each of the probing sequences is preferably of an identical sequence, thereby causing the probes to selectively hybridize only to portions of the biomolecule fragment 20 that have a complementary sequence. Unlike the embodiment of FIG. 5, however, in this embodiment, each probe 70 includes a probe sequence 10 and a tag 80 connected to the 5' end of each probe sequence 10 by a linker 90. In the embodiment shown, the tag 80 may comprise a dsDNA segment, however, any of a wide variety of tags known to those skilled in the art may be employed. The tags make current fluctuations in sequencing systems more noticeable as the hybridized probes translocate through the system. In addition, different tags may be used to help distinguish among the different probes. These tags may be proteins, double-stranded DNA, single-stranded DNA or other molecules.

Figure 6A:
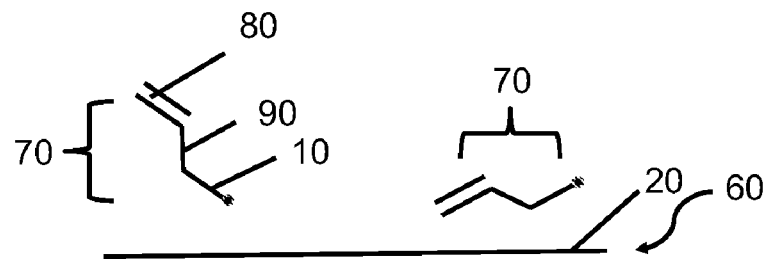
FIGS. 6(a)-6(d) are a schematic depiction of an assay method in accordance with an embodiment of the invention in which tagged ssDNA probes are bound to a single-stranded DNA or RNA analyte, a base extension reaction is carried out, and a binding moiety which binds to single-stranded portions of the resulting analyte is employed.

The biomolecule fragment 20 to be analyzed and probes 70 are depicted prior to hybridization in FIG. 6(a).

Figure 6B:
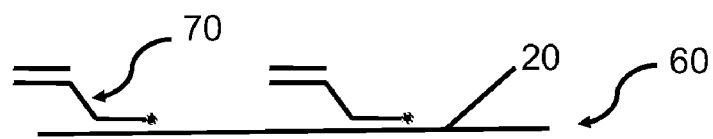

The analyte 60 is shown in FIG. 6(b) following hybridization of the probes 70 to the biomolecule fragment 20. The resulting structure is a biomolecule fragment having, where hybridization has occurred, duplex domains. The double stranded domains are of a length corresponding to the length of the probe sequences 10. Thus, in a case where a 6-mer probe sequence is employed, the analyte 60 will comprise a single-stranded structure having a plurality of 6-mer duplex regions, formed by the hybridized probes.

Figure 6C:
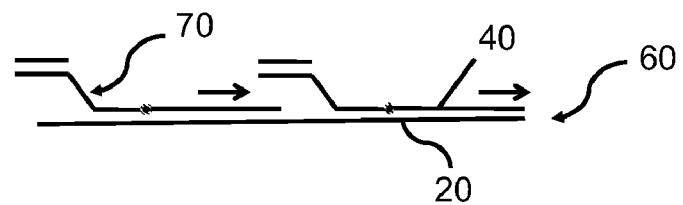

Following the hybridization step, a base extension reaction is performed as depicted in FIG. 6(c). As in the prior example, the hybridized probes 70 are extended from the 3' ends of the probe sequences 10 along the biomolecule fragment 20 to create duplex regions 40 on the analyte in single-stranded gaps of that had previously existed between the probe locations. Note, however, that as before, the base extension reaction is intended to be limited in scope. Rather than extending from the 3' end of each probe to the 5' end of an adjacent probe, the base extension reaction is intended to be terminated such that single-stranded segments remain on the analyte 60 before the 5' end of each probe sequence 10. The resulting analyte 60 structures, like those of FIG. 6(b), comprise duplex regions alternating with single-stranded regions. However, unlike the structures of FIG. 6(b), the resulting structures are characterized as being primarily duplexes with small single-strand gaps.

Figure 6D:
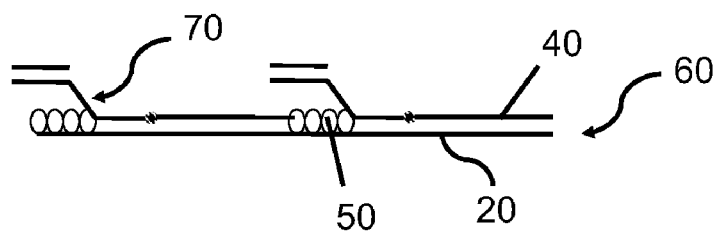

Finally, as depicted in FIG. 6(d), a binding moiety 50, which is selective to the single-strand regions, is reacted with the analyte 60 in a manner such that the binding moiety fills the single-stranded gaps in the analyte. Although it is preferred that the binding moiety 50 be distinguishable from duplex regions when the analyte is introduced to a nanopore or micro- or nanochannel sequencing system, since this embodiment uses tags to enhance detection of the probes, the requirement is less stringent than in that of FIG. 5. As before, by detecting the binding moiety and/or the tags, the locations of the probes on the analyte may be determined. Since the positions of the probes may be readily determined, and as the analyte portions containing the probes will have regions complementary to the known probe sequences, one may map the sequence and location of specific domains on the analyte. The resulting maps may be combined and utilized to determine broader sequence information for the analyte.

Figure 7A:
FIGS. 7(a)-7(f) are a schematic depiction of an assay method in accordance with an embodiment of the invention in which RNA probes are bound to a single-stranded DNA analyte, a base extension reaction is carried out, the RNA probes are removed, and a binding moiety which binds to single-stranded portions of the resulting analyte is employed.

Another embodiment is depicted in FIGS. 7(a)-7(f). In FIG. 7(a), the analyte 25 comprising a single-stranded DNA fragment 20 is exposed to RNA probes 35. Each probe 35 is a short RNA fragment of a known sequence. The probes 35 may be of any length depending on the number of bases that they include. As before, each of the probes is preferably of an identical sequence, although probe mixtures of two or more sequences are envisioned as well. The probes selectively hybridize only to portions of the ssDNA fragment 20 that have a complementary sequence. The ssDNA fragment 20 and RNA probes 35 are depicted prior to hybridization in FIG. 7(a).

Figure 7B:
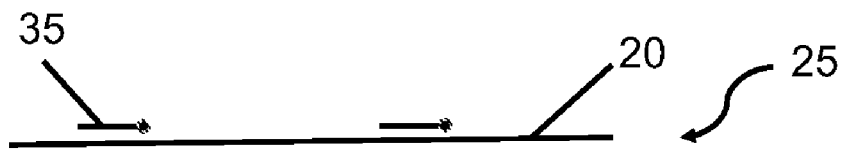

The analyte 25 is shown in FIG. 7(b) following hybridization of the RNA probes 35 to the biomolecule fragment 20. The resulting structure is a ssDNA fragment having duplex domains where hybridization has occurred. The duplex domains are of a length corresponding to the length of the RNA probes 35. Thus, in a case where a 6-mer probe is employed, the analyte 25 will include a plurality of 6-mer duplex regions, formed by the hybridized probes.

Figure 7C:
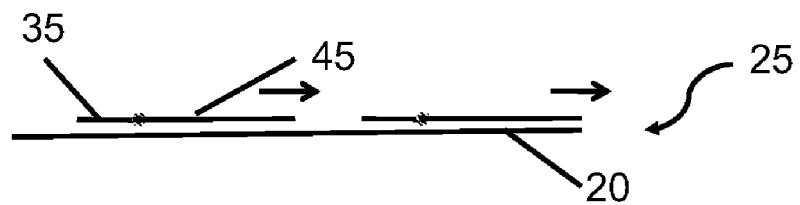
Figure 7D:
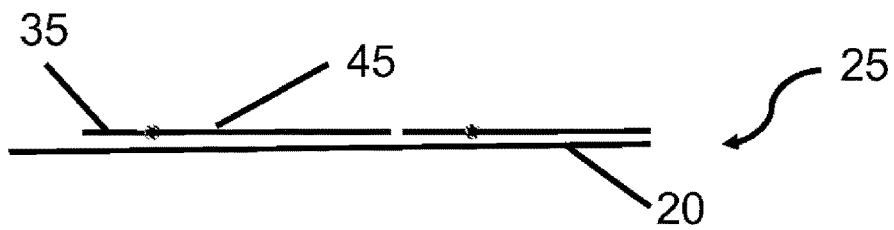
Figure 7E:
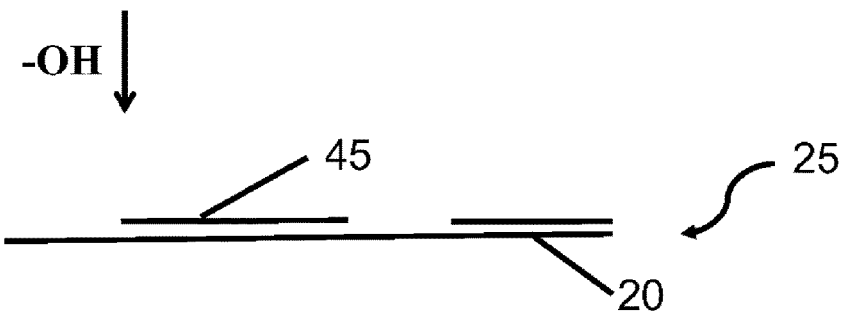

Following the hybridizing step, a DNA base extension reaction is performed as depicted in FIG. 7(c). Specifically, the extension runs from the 3' ends of the RNA probes 35 along ssDNA fragment 20 to create duplex regions 45 on the analyte in gaps that had previously existed between the probe locations. Unlike the base extension reaction of FIGS. 5 and 6 above, however, the base extension reaction may be allowed to proceed from the 3' end of each probe to the 5' end of an adjacent probe as shown in FIG. 7(d). The resulting analyte 25 structure includes duplex regions of double-stranded DNA (dsDNA) 45 resulting from the base extension reaction, alternating with regions of RNA/DNA duplexes 35 in regions where the RNA probes hybridized to the ssDNA analyte.

The analyte 25 of FIG. 7(d) is then reacted with a hydroxyl ion (—OH) which denatures and decomposes the RNA probes. The resulting analyte shown in FIG. 7(e) includes dsDNA regions 45 separated by gaps formed where the RNA probes had previously hybridized to the ssDNA analyte.

Figure 7F:
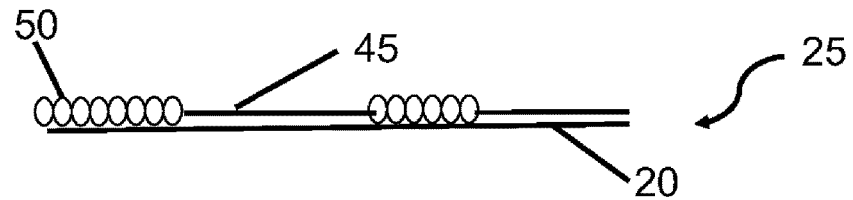
Figure 8A:
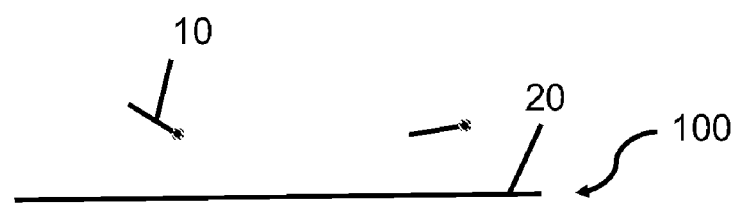
FIGS. 8(a)-8(c) are a schematic depiction of an assay method in accordance with an embodiment of the invention in which oligonucleotide probes are bound to a single-stranded DNA or RNA analyte, and a binding moiety is bound to duplex structures formed by the probes.
Figure 8B:
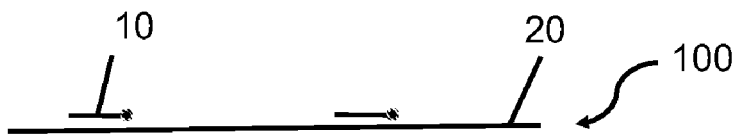
Figure 8C:
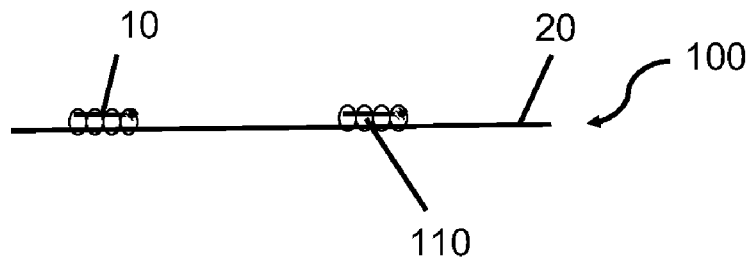

Finally, as depicted in FIG. 7(f), a binding moiety 50 which is selective to ssDNA regions, is reacted with the analyte 25 in a manner such that the binding moiety fills the ssDNA gaps in the analyte. Thus, the RNA probes are removed to allow the reaction of the binding moiety 50 with the analyte 25, to thereby prepare the biomolecule analyte, i.e., the target analyte. The binding moiety is distinguishable from the double-stranded regions, and is typically easier to detect than a single-stranded region. Moreover, the binding moiety 50 is typically easier to detect than an RNA probe 35. The described method, therefore, facilitates the detection of sites to which the RNA probes 35 hybridize. Another embodiment is depicted in FIGS. 8(a)-8(c), where the analyte 100 is formed from a ssDNA or RNA biomolecule fragment 20 exposed to single-stranded oligonucleotide probes 10. As stated above, each probe 10 is a short ssDNA or RNA segment of a known sequence. The probes 10 may be of any length depending on the number of bases that they include. As before, each of the probes is preferably of an identical sequence, thereby causing the probes to selectively hybridize only to portions of the biomolecule fragment 20 that have a complementary sequence. The biomolecule fragment 20 and probes 10 are depicted prior to hybridization in FIG. 8(a).

The analyte 100 is shown in FIG. 8(b) following hybridization of the probes 10 to the biomolecule fragment 20. The resulting structure is a single-stranded biomolecule fragment having, where hybridization has occurred, duplex domains. The duplex domains are of a length corresponding to the length of the probes. Thus, in a case where a 6-mer probe is employed, the analyte 100 will include a plurality of 6-mer duplex regions, formed by the hybridized probes.

Next, unlike the embodiments of FIGS. 5-7, no base extension reaction is used. Rather, a binding moiety 110 with a selectivity for duplex domains is employed. Suitable compositions include proteins such as enzymes that lack a cofactor. Examples include restriction enzymes that are added in the absence of $Mg^{2+}$. Lacking the Mg ion, the protein will bind to duplex domains but be unable to cut. In other embodiments, polymerases can be used in the absence of $Mg^{2+}$ or nucleoside triphosphates may be used. Likewise, topoisomerases could be added in the absence of $Mg^{2+}$. Regardless of the specific duplex selective entity, as shown in FIG. 8(c), the binding moiety 110 selectively binds to the analyte 100 only at duplex regions on the analyte 100, thereby enhancing detection of these regions when the analyte is introduced to a nanopore or micro- or nanochannel sequencing system. As before, this allows determination of the locations of probe binding, and provides both location and sequence information for the analyte.

Figure 9A:
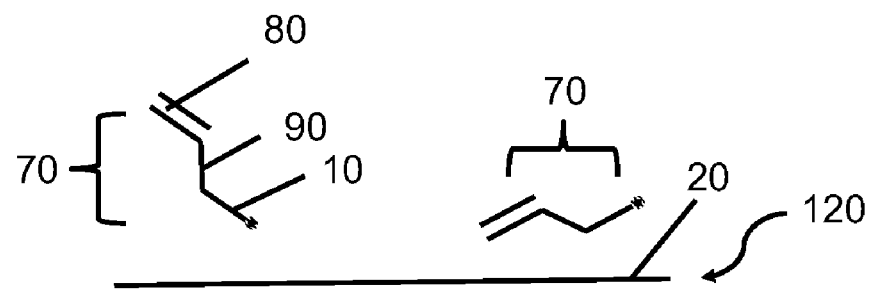
FIGS. 9(a)-9(c) are a schematic depiction of an assay method in accordance with an embodiment of the invention in which tagged oligonucleotide probes are bound to a single-stranded DNA or RNA analyte, and a binding moiety is bound to duplex structures formed by the probes.
Figure 9B:
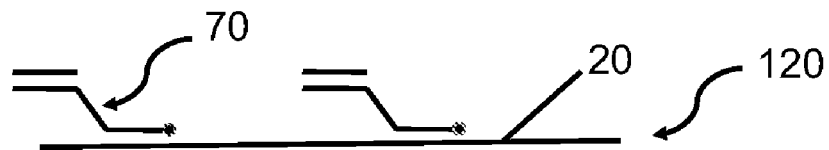
Figure 9C:
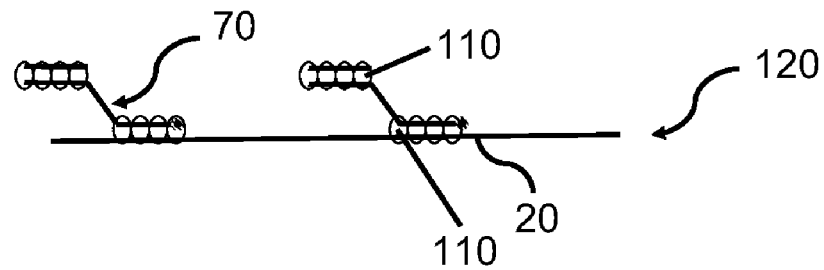

Similarly, in FIGS. 9(a)-9(c), the analyte 120 is formed from a single-stranded biomolecule fragment 20 exposed to tagged single-stranded oligonucleotide probes 70. As in FIG. 6, each tagged probe 70 is a short segment of ssDNA or RNA, (i.e., a probe or probing segment), 10 of a known sequence. The probing segments 10 may be of any length depending on the number of bases that they include. As before, each of the probing sequences is preferably of an identical sequence, thereby causing the probes to selectively hybridize only to portions of the biomolecule fragment 20 that have a complementary sequence. Each probe includes a probe sequence 10 and a tag 80 connected the 5' end of the probe sequence 10 by a linker 90. As before, the tag 80 may comprise a dsDNA segment, however, any of a wide variety of tags known to those skilled in the art may be employed. The biomolecule fragment 20 to be analyzed and probes 70 are depicted prior to hybridization in FIG. 9(a).

The analyte 120 is shown in FIG. 9(b) following hybridization of the probes 70 to the biomolecule fragment 20. The resulting structure is a biomolecule fragment having, where hybridization has occurred, tagged duplex domains thereon.

The duplex domains are of a length corresponding to the length of the probe sequences 10. Thus, in a case where a 6-mer probe sequence is employed, the analyte 120 will include a plurality of tagged 6-mer duplex regions, formed by the hybridized tagged probes.

As is shown in FIG. 9(c), the analyte 120 has been reacted with a binding moiety 110 with a selectivity for duplex structures. The binding moiety 110 selectively binds to the analyte 120 only at regions hybridized to probe sequences 10, and, if duplex tags are employed, at the tags, thereby enhancing detection of these regions when the analyte is introduced to a nanopore or micro- or nanochannel sequencing system. As before, this allows determination of the locations of probe binding, and provides both location and sequence information for the analyte.

Figure 10A:
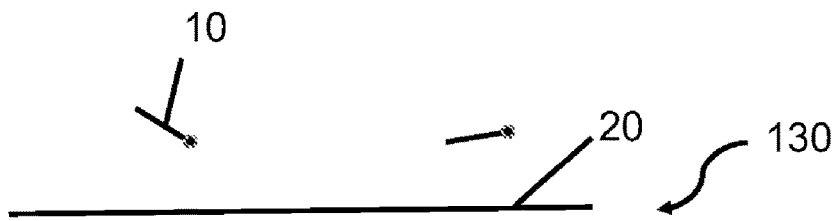
FIGS. 10(a)-10(c) are a schematic depiction of an assay method in accordance with an embodiment of the invention in which oligonucleotide probes are bound to a single-stranded DNA or RNA analyte, and a binding moiety is bound to the analyte in gaps between the probes.
Figure 10B:
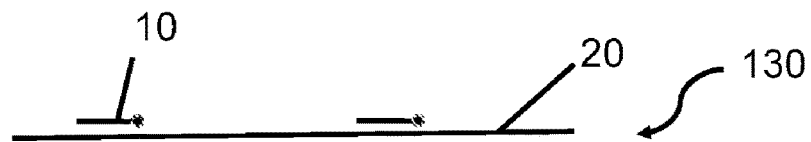
Figure 10C:
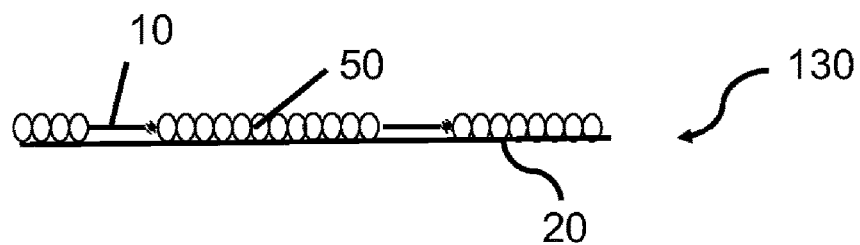

Another embodiment, depicted in FIGS. 10(a)-10(c), is similar to that shown in FIG. 5, but without the use of a base extension reaction. In FIG. 10, the analyte 130 is formed from an ssDNA or RNA fragment 20 exposed to single-stranded oligonucleotide probes 10. As stated above, each probe 10 is of a known sequence. As before, each of the probes is preferably of an identical sequence, thereby causing the probes to selectively hybridize only to portions of the biomolecule fragment 20 that have a complementary sequence. The biomolecule fragment 20 and probes 10 are depicted prior to hybridization in FIG. 10(a).

The analyte 130 is shown in FIG. 10(b) following hybridization of the probes 10 to the biomolecule fragment 20. The resulting structure is a single-stranded fragment having, where hybridization has occurred, duplex domains. The duplex domains are of a length corresponding to the length of the probes. Thus, in a case where a 6-mer probe is employed, the analyte 130 will comprise a single-stranded biomolecule fragment having a plurality of 6-mer duplex regions, formed by the hybridized probes.

In FIG. 10(c), a binding moiety 50 with a selectivity for duplex regions is employed as described above. A base extension reaction is not used. Suitable binding moieties have been described previously. As is shown in FIG. 10(c), the binding moiety 50 selectively binds to the analyte 130 only at single-stranded regions on the analyte 130, thereby enhancing detection of these regions when the analyte is introduced to a nanopore or micro- or nanochannel sequencing system. As before, this allows determination of the locations of probe binding, and provides both location and sequence information for the analyte.

Mapping of target analytes prepared using the methods of embodiments of the present invention may be carried out using electrical detection methods employing nanopores, nano-channels or micro-channels using the methods described in U.S. patent application Ser. No. 12/789,817.

Figure 11A:
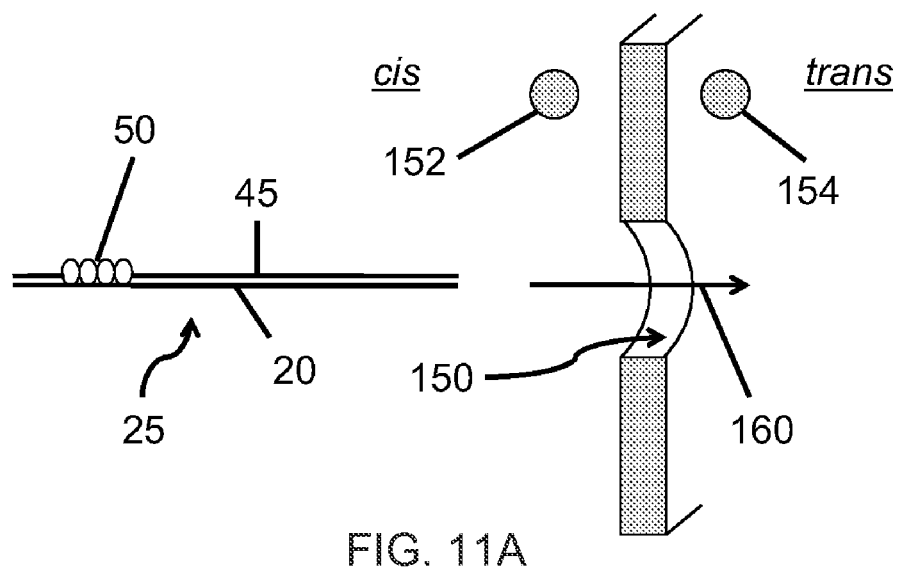
FIG. 11(a) is a schematic depiction of an assay method in accordance with an embodiment of the invention showing a DNA molecule having a binding moiety region in a nanopore apparatus.

In one embodiment, current is measured during translocation of a DNA strand through a nanopore as shown in FIG. 11(a). When used in embodiments of the present invention, nanopores may have a diameter selected from a range of about 1 nm to about 1 µm. More preferably the nanopore has a diameter that is between about 2.3 nm and about 100 nm. Even more preferably the nanopore has a diameter that is between about 2.3 nm and about 50 nm.

Specifically, for nanopore 150, a measurable current produced by electrodes 152, 154 runs parallel 160 to the movement of the target analyte 25. In this example, the target analyte 25, i.e., biomolecule analyte, is made using the method depicted in FIGS. 7(a)-7(f), however any of the methods and analytes of embodiments of the present invention could be used. The target analyte 25 includes a single-stranded DNA fragment 20 having a duplex region 45 and a binding moiety 50 present at non-duplexed regions. Variations in current are a result of the relative diameter of the target analyte 25 as it passes through the nanopore 150. A relative increase in volume of the target analyte 25 passing through the nanopore 150 causes a temporary interruption or decrease in the current flow through the nanopore, resulting in a measurable current variation. Portions of the target analyte 25 including the binding moiety 50 are larger in diameter than portions of the target analyte that do not include the binding moiety 50. As a result, when the binding moiety 50 passes through the nanopore 150, further interruptions or decreases in the current flow between electrodes 152, 154 occurs. This is depicted in the waveform 200 in FIG. 11(b).

Figure 11B:
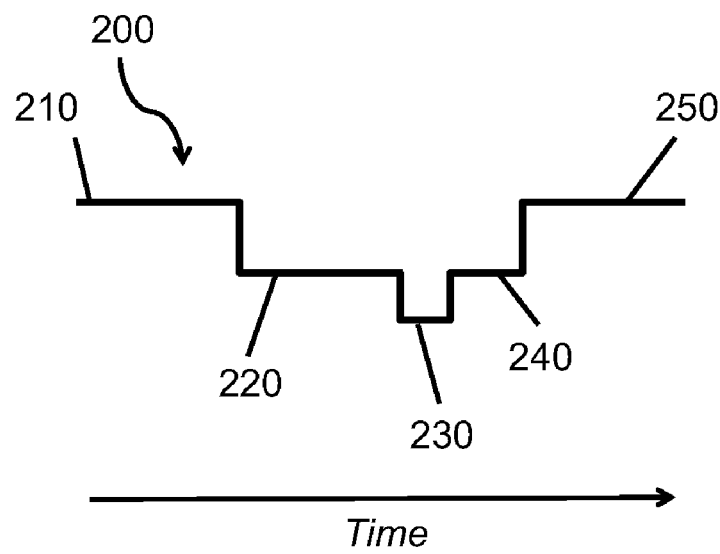
FIG. 11(b) is a schematic depiction of an assay method in accordance with an embodiment of the invention showing a current measurement waveform as a DNA molecule having a binding moiety region translocates through the nanopore apparatus of FIG. 11(a).

In FIG. 11(b), the waveform 200 may be interpreted as follows. Current measurement 210 represents measured current prior to passage of the target analyte 25, i.e., biomolecule analyte, through the nanopore 150 from the cis side to the trans side. As the target analyte 25 enters the nanopore 150, from the cis side of the nanopore, the current is partially interrupted forming a first trough 220 in the recorded current. Once the binding moiety 50 on the target analyte 25 enters the nanopore 150, a further decrease in current occurs, causing a deeper, second trough 230 in the current measurement. Upon passage of the binding moiety 50 entirely through the nanopore 150, a distal portion of the target analyte 25 may remain in the nanopore. This causes the measured current 240 to rise to approximately the level of the first trough 220. Finally, once the entire target analyte has passed completely through the nanopore 150 to the trans side, the measured current 250 returns to a level approximating that of the initial level 210. The current variation measurements are recorded as a function of time. As a result, the periodic variations in current indicate where, as a function of relative or absolute position, the regions of binding moiety 50 are formed on the target analyte 25. Since the binding moiety is present at recognition sites for specific probes, the relative or absolute position of the specific sequences associated with each probe may be determined. This allows mapping of those specific sequences on the target analyte. Multiple maps and sequence information produced using multiple probes may be generated.

Figure 12:
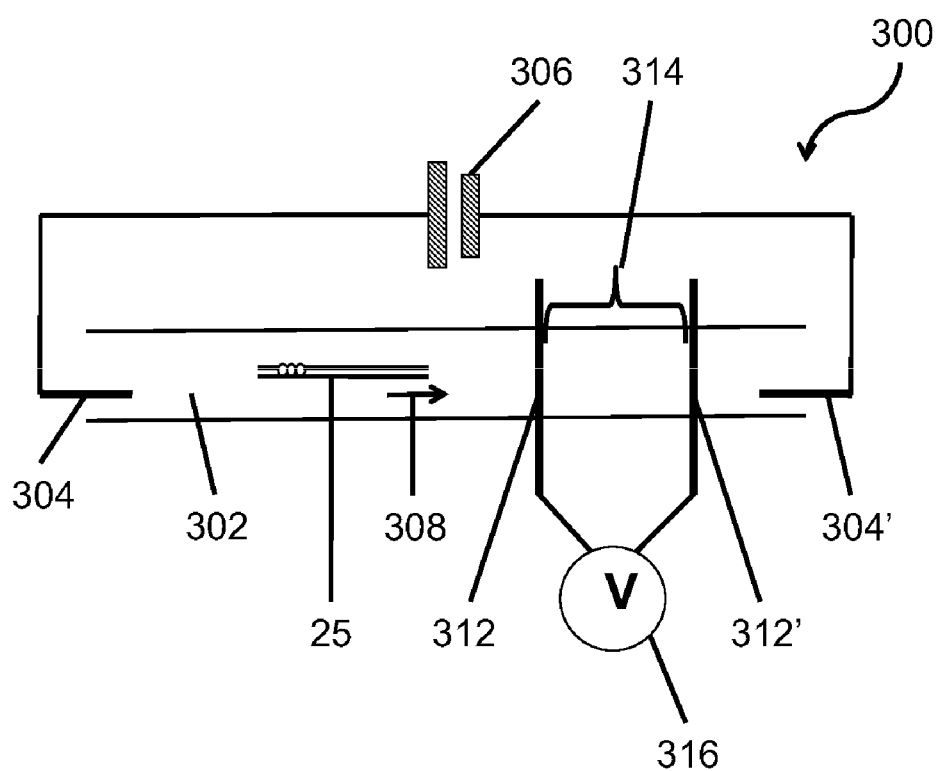
FIG. 12 is a schematic depiction of an assay method in accordance with an embodiment of the invention showing a nano-channel or micro-channel apparatus useful for mapping the analytes of the present invention.
Figure 13A:
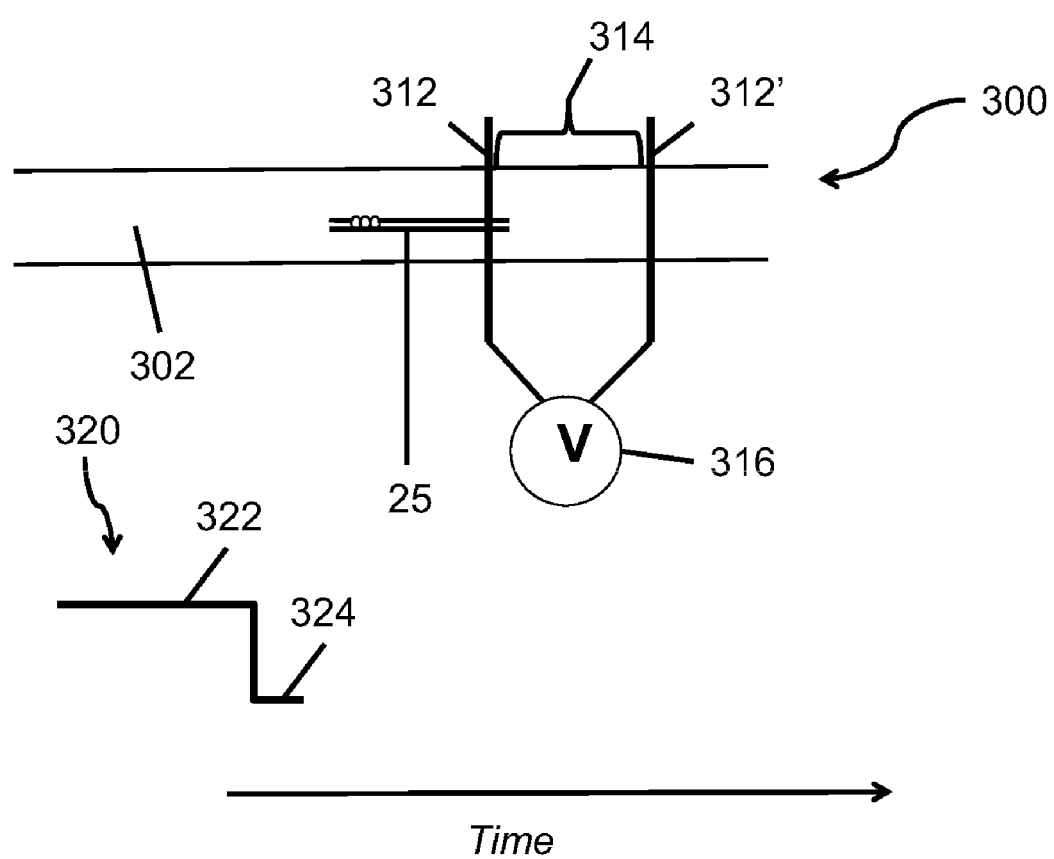
FIG. 13(a) is a schematic depiction of an assay method in accordance with an embodiment of the invention showing an electrical potential measurement as a DNA molecule having a binding moiety region enters a detection volume in the apparatus of FIG. 12.
Figure 13B:
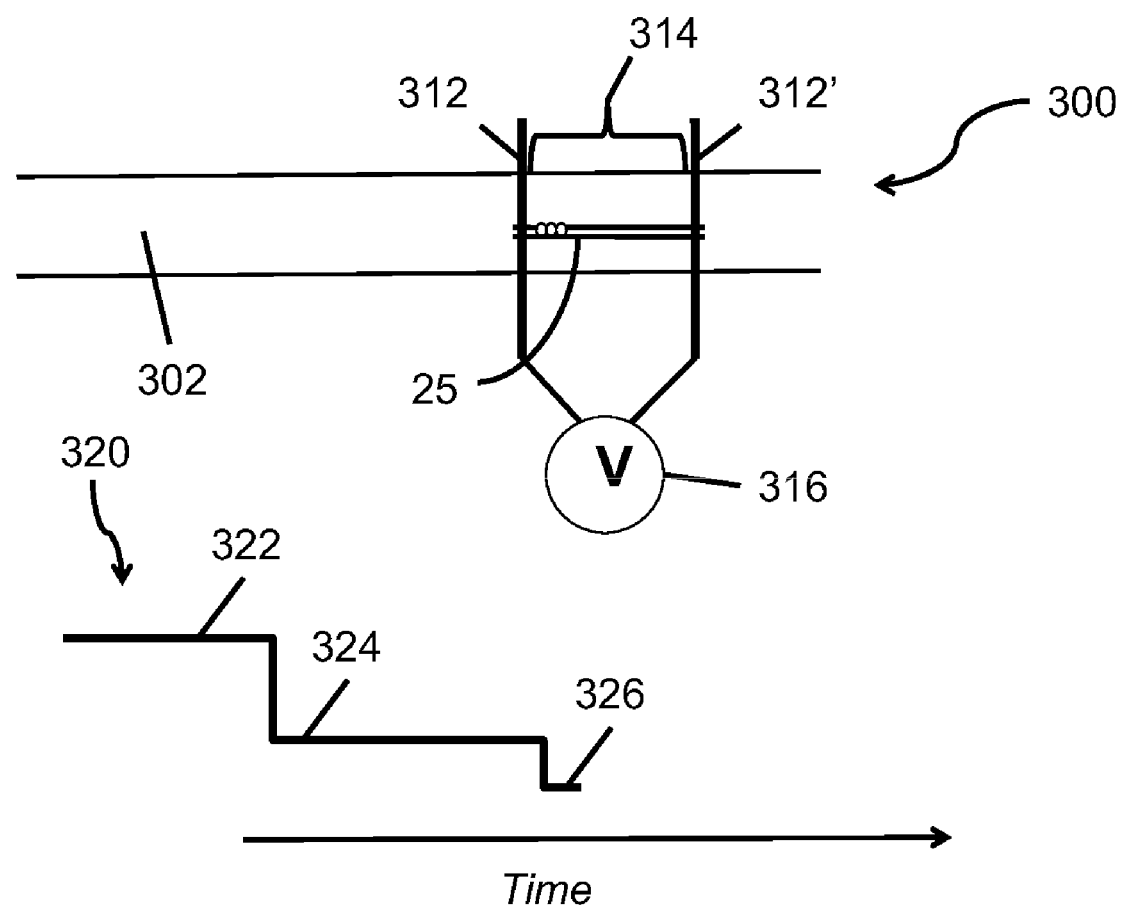
FIG. 13(b) is a schematic depiction of an assay method in accordance with an embodiment of the invention showing an electrical potential measurement as a binding moiety region on a DNA molecule enters a detection volume in the apparatus of FIG. 12.
Figure 13C:
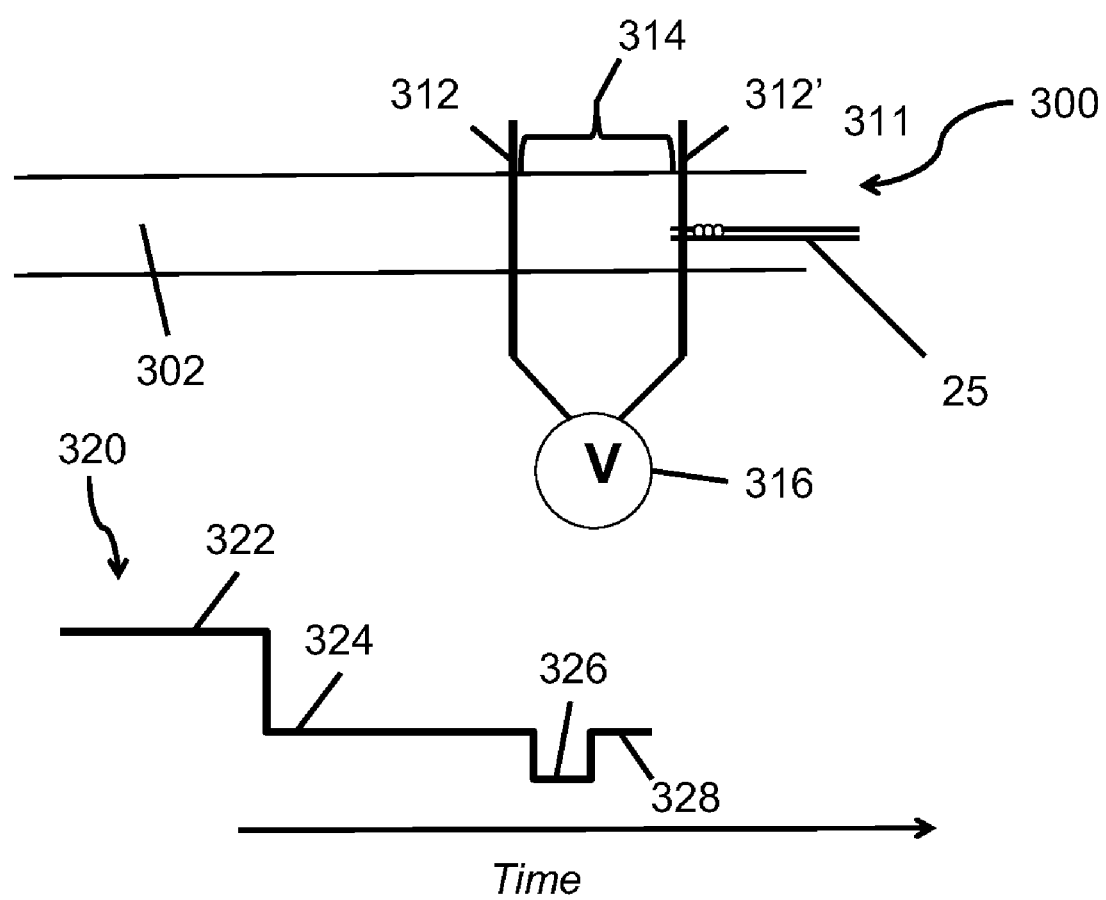
FIG. 13(c) is a schematic depiction of an assay method in accordance with an embodiment of the invention showing an electrical potential measurement as a binding moiety region on a DNA molecule exits a detection volume in the apparatus of FIG. 12.
Figure 13D:
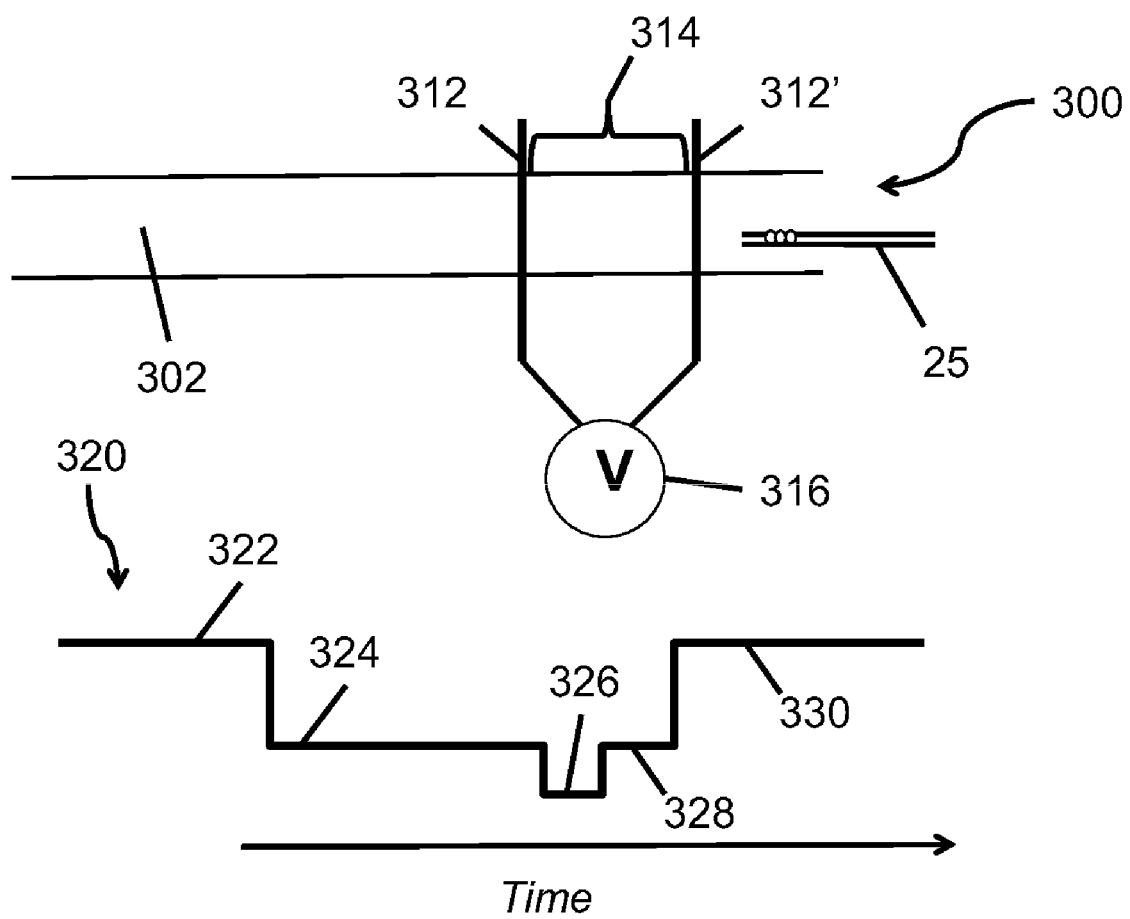
FIG. 13(d) is a schematic depiction of an assay method in accordance with an embodiment of the invention showing an electrical potential measurement as a DNA molecule having a binding moiety region exits a detection volume in the apparatus of FIG. 12.
Figure 14:
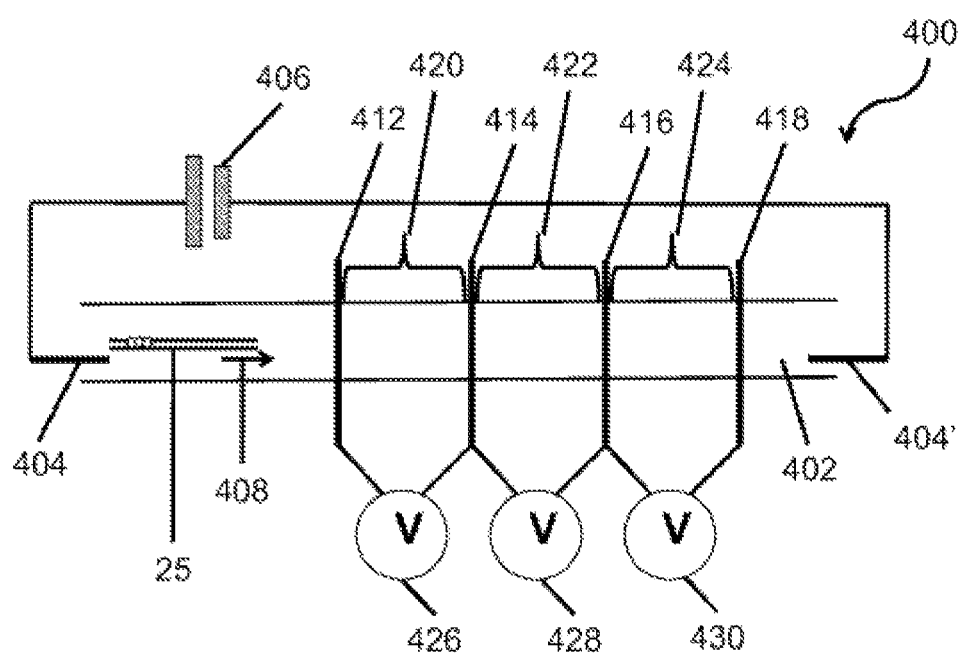
FIG. 14 is a schematic depiction of an assay method in accordance with an embodiment of the invention showing a nano-channel or micro-channel apparatus having multiple detection volumes.

In another embodiment, an electrical property such as electrical potential or current is measured during translocation of a DNA strand through a nano-channel or micro-channel as shown in FIGS. 12 through 14. One embodiment of a fluidic channel apparatus is shown schematically in FIG. 12. In FIG. 12, the apparatus 300 includes a fluidic micro-channel or nano-channel 302. The fluidic channel may be a micro-channel having a width selected from a range of about 1 µm to about 25 µm or a nano-channel having a width selected from a range of about 10 nm to about 1 µm. In the case of a micro-channel, the depth may be selected from a range of about 200 nm to about 5 µm, whereas in the case of a nano-channel, the depth may be selected from a range of about 10 nm to about 1 µm. In either case, the channel may have a length selected from a range of about 1 µm to about 10 cm.

A first pair of electrodes 304, 304' is connected to a current source 306 and positioned in a spaced apart relationship in the channel. These electrodes provide an electrical current along the channel and may be used to provide or enhance a driving force 308 to a target analyte 25, i.e., biomolecule analyte, in the channel. Other driving forces such as pressure or chemical gradients are contemplated as well. A second pair of electrodes 312, 312', i.e., detector electrodes, is positioned preferably substantially perpendicular to the channel in a spaced apart relationship to define a detection volume 314. The second pair of electrodes 312, 312', is connected to a detector 316, such as a voltmeter, which monitors an electrical property in the detection volume 314. In the embodiment where the detector 316 is a voltmeter, a drop in electrical potential, produced by the first pair of electrodes 304, 304', is measured across the detection volume 314. As in the case of the nanopore apparatus, in this example, a target analyte 25 is made using the method depicted in FIGS. 7(a)-7(f), however any of the methods and analytes of embodiments of the present invention could be used.

The operation of the device is depicted schematically in FIGS. 13(a)-13(d). In FIGS. 13(a)-13(d), the first pair of electrodes 304, 304' and the current source 306 have been omitted for clarity. In FIG. 13(a), the fluidic channel 302 contains a target analyte 25, i.e., biomolecule analyte, traveling therethrough. An electrical property, in this case electrical potential, is measured and recorded across the detection volume 314 by the detector electrodes 312, 312' and the detector 316. In the embodiment depicted, the target analyte 25 is that of FIGS. 7(f) and 14; i.e., it includes a single-stranded DNA fragment having a duplex region and a binding moiety present at non-duplexed regions.

Prior to the entry of the analyte 25 into the detection volume 314, a substantially constant voltage 322 is measured across the detection volume. This voltage is shown in the waveform 320 of FIG. 13(a). As the analyte 25 enters the detection volume 314, it causes an interruption or decrease in the electrical property measured in the detection volume. This interruption or decrease causes a first trough 324 to be exhibited in the waveform 320.

FIG. 13(b) shows the device and waveform 320 once the portion of the analyte 25 including the binding moiety has entered the detection volume 314. Due to its increased volume, entry of the binding moiety into the detection volume 314 causes a further interruption or decrease in the electrical property measured in the detection volume. This further interruption or decrease causes a second trough 326 to be exhibited in the waveform 320.

In FIG. 13(c), the portion of the analyte 25 containing the binding moiety has exited the detection volume 314; however, a distal portion of the analyte 25 may still be present in the detection volume. As a result, the waveform 320 has returned to a level 328 approximating that detected when the initial portion of the analyte first entered the detection volume.

Finally, as shown in FIG. 13(d), the analyte 25 has fully exited the detection volume 314. As a result, the waveform 320 has returned to a level 330 approximating that detected prior to initial entry of the analyte into the detection volume.

Another embodiment of a fluidic channel apparatus is shown in FIG. 14. In FIG. 14, the apparatus 400 includes a fluidic micro-channel or nano-channel 402. As before, the fluidic channel may be a micro-channel having a width selected from a range of about 1 µm to about 25 µm or a nano-channel having a width selected from a range of about 10 nm to about 1 µm. In the case of a micro-channel, the depth may be selected from a range of about 200 nm to about 5 µm, whereas in the case of a nano-channel, the depth may be selected from a range of about 10 nm to about 1 µm. In either case, the channel may have a length selected from a range of about 1 µm to about 10 cm.

A first pair of electrodes 404, 404' is connected to a current source 406 and positioned in a spaced apart relationship in the channel. These electrodes provide an electrical current along the channel and may be used to provide or enhance a driving force 408 to an analyte 25 in the channel. Other driving forces such as pressure or chemical gradients are contemplated as well. Multiple detector electrodes 412, 414, 416, 418, are positioned preferably perpendicular to the channel in a spaced apart relationship to define a plurality of detection volumes between adjacent detector electrodes. Thus, as seen in FIG. 16, detector electrodes 412 and 414 define detection volume 420, detector electrodes 414 and 416 define detection volume 422, and detector electrodes 416 and 418 define detection volume 424. The detector electrodes are each connected to detectors 426, 428, 430 such as voltmeters, which monitor an electrical property in each detection volume. In the embodiment where the detectors are voltmeters, a drop in electrical potential is measured across each detection volume. Operation of the apparatus is similar to that of the system of FIG. 12, with the exception that additional waveforms are generated due to the presence of additional detection volumes. The additional waveforms may be combined to further improve the quality of the data being generated by the device.

It should be understood that number of detector electrodes and detection volumes is not intended to be limited to those depicted in FIG. 14. Rather, any number of detection volumes may be included along the length of the fluidic channel. Further, the detector electrodes and detection volumes need not be evenly spaced, evenly sized or directly adjacent to one another. Various detection volume sizes, spacing and configurations are contemplated.

Both the nanopore apparatus and the fluidic channel apparatus allow detection of an analyte as well as detection of a binding moiety present on the analyte. Furthermore, relative or absolute positional information of the binding moiety may be obtained. Since, in each of the embodiments depicted herein, the relative or absolute position of the binding moiety is, at the very least, suggestive of the relative or absolute position of a known probe, embodiments of the invention allow determination of the location of the known recognition sequence of the probe. This in turn, allows the biomolecule to be mapped. The repeated use of different probes allows greater complexity, i.e., multiple recognition sequences, to be combined. Multiple maps and sequence information produced using multiple probes may be generated.

EQUIVALENTS

Those skilled in the art will readily appreciate that all parameters listed herein are meant to be exemplary and actual parameters depend upon the specific application for which the methods and materials of embodiments of the present invention are used. It is, therefore, to be understood that the foregoing embodiments are presented by way of example only and that, within the scope of the appended claims and equivalents thereto, the invention may be practiced otherwise than as specifically described.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A method for preparing a biomolecule analyte, said biomolecule analyte comprising a single-stranded human DNA or human RNA template, at least two identical, oligonucleotide probes hybridized to the single-stranded human DNA or human RNA template, and a binding moiety coating a portion of the single-stranded human DNA or human RNA template, the method comprising:
   a. providing the single-stranded human DNA or human RNA template;
   b. hybridizing a first plurality of identical, oligonucleotide probes to the template, each probe having 4 to 12 bases and a 5' end and a 3' end, to thereby form an analyte having at least one single-stranded region and at least two duplex regions, each duplex region comprising one of the probes hybridized to a complementary portion of the template, wherein one of the at least one single-stranded regions is disposed between two duplex regions;
   c. conducting a base-extension reaction in the at least one single-stranded region from the 3' end of a hybridized probe abutting the at least one single-stranded region toward the 5' end of an adjacent hybridized probe abutting the at least one single-stranded region, wherein the base extension reaction comprises adding mononucleotides complementary to the template to extend the duplex region defined by the hybridized probe;
   d. terminating the base-extension reaction under termination conditions such that at least one of the remaining single-stranded regions is adjacent to the 5' end of the adjacent hybridized probe; and
   e. reacting the analyte formed in step d with a binding moiety consisting essentially of a protein that selectively coats and binds to the at least one remaining single-stranded region to thereby prepare the biomolecule analyte, wherein the binding moiety coats single-stranded DNA or RNA selectively with respect to double-stranded regions.

2. The method of claim 1, wherein the probes comprise single-stranded DNA.

3. The method of claim 1, wherein the probes comprise RNA.

4. The method of claim 1, wherein the base extension reaction is performed by a DNA or RNA polymerase.

5. The method of claim 1, wherein at least a portion of the probes in the first plurality of probes has attached thereto a detectable tag.

6. The method of claim 1, wherein the biomolecule analyte is configured for detection of positional information in a nanopore system having a nanopore with a diameter from 1 nm to 1 µm, and a pair of electrodes disposed on either side of the nanopore, thereby being configured to produce a current parallel to movement of the biomolecule analyte and to detect changes in an electrical property indicative of the presence of the analyte and probes as they transit the nanopore, the pair of electrodes being in communication with an electrical signal detector and data collection device programmed to respectively detect and record changes in an electrical property in the nanopore as the target biomolecule translocates through the nanopore.

7. The method of claim 6, further comprising:
   generating with the nanopore system a waveform indicative of changes in an electrical property across the nanopore as the biomolecule analyte is translocated therethrough, the changes in the electrical property being indicative of regions including or lacking the binding moiety.

8. The method of claim 1, wherein the biomolecule analyte is configured for detection of positional information in a fluidic channel system, the fluidic channel system comprising (i) a micro-channel having a width from 1 µm to 25 µm, a depth from 200 nm to 5 µm and a length of 1 µm to 10 cm, or a nano-channel having a width from 10 nm to 1 µm, a depth from 10 nm to 1 µm and a length of 1 µm to 10 cm, (ii) a pair of electrodes laterally offset from each other along the microchannel and defining a detector volume therebetween and in communication with an electrical signal detector and data collection device programmed to respectively detect and record changes in an electrical property in the detector volume as the target biomolecule translocates through the detector volume, and (iii) a driving force generator for translocating the target biomolecule through the detector volume.

9. The method of claim 8, further comprising:
generating with the fluidic channel system a waveform indicative of changes in an electrical property across a fluidic channel as the biomolecule analyte is translocated therethrough, the changes in the electrical property being indicative of regions including or lacking the binding moiety.

10. The method of claim 1, wherein the oligonucleotide probes comprise oligonucleotide analog probes selected from the group consisting of LNAs, PNAs and 2'-methoxy nucleotide analogs.

11. The method of claim 1, wherein the first plurality of identical, oligonucleotide probes is replaced by a pool of oligonucleotide probes comprising at least a first plurality of identical, oligonucleotide probes and a second plurality of identical, oligonucleotide probes, wherein the probes of the second plurality are different from the probes of the first plurality.

12. A method for preparing a biomolecule analyte, said biomolecule analyte comprising a single-stranded human DNA or human RNA template, at least two identical, oligonucleotide probes hybridized to the single-stranded human DNA or human RNA template, and a binding moiety coating a portion of the single-stranded human DNA or human RNA template, the method comprising:
f. providing the single-stranded human DNA or human RNA template;
g. hybridizing a first plurality of identical, oligonucleotide probes to the template, each probe having 4 to 12 bases and a 5' end and a 3' end, to thereby form an analyte having at least one single-stranded region and at least two duplex regions, each duplex region comprising one of the probes hybridized to a complementary portion of the template, wherein one of the at least one single-stranded regions is disposed between two duplex regions;
h. conducting a base-extension reaction in the at least one single-stranded region from the 3' end of a hybridized probe abutting the at least one single-stranded region toward the 5' end of an adjacent hybridized probe abutting the at least one single-stranded region, wherein the base extension reaction comprises adding mononucleotides complementary to the template to extend the duplex region defined by the hybridized probe;
i. terminating the base-extension reaction under termination conditions such that at least one of the remaining single-stranded regions is adjacent to the 5' end of the adjacent hybridized probe; and
j. reacting the analyte formed in step d with a binding moiety consisting essentially of a protein that selectively coats and binds to the at least one remaining single-stranded region to thereby prepare the biomolecule analyte, wherein (i) the binding moiety coats single-stranded DNA or RNA selectively with respect to double-stranded regions and (ii) said protein comprises one or more proteins selected from the group consisting of RecA, T4 gene 32 protein, f1 geneV protein, human replication protein A, Pf3 single-stranded binding protein, adenovirus DNA binding protein, and *E. coli* single-stranded binding protein.

13. A method for preparing a biomolecule analyte, said biomolecule analyte comprising a single-stranded human DNA template, at least two identical RNA probes hybridized to the single-stranded DNA template, and a binding moiety coating a portion of the single-stranded DNA template, the method comprising:
a. providing the single-stranded DNA template;
b. hybridizing a first plurality of identical RNA probes to the template, each probe having 4 to 12 bases and a 5' end and a 3' end, to thereby form an analyte having at least one single-stranded region and at least two duplex regions, each duplex region comprising one of the probes hybridized to a complementary portion of the template, wherein one of the at least one single-stranded regions is disposed between two duplex regions;
c. conducting a base extension reaction in the at least one single-stranded region from the 3' end of the hybridized probe abutting the at least one single-stranded region toward the 5' end of an adjacent hybridized probe abutting the at least one single-stranded region, wherein the base extension reaction comprises adding mononucleotides complementary to the template to extend the duplex region defined by the hybridized probe;
d. allowing the base-extension reaction to fill each single-stranded region disposed between two duplex regions on the analyte;
e. removing the RNA probes to provide the analyte with at least one single-stranded segment in the region to which an RNA probe had been hybridized; and
f. reacting the analyte formed in step e with a binding moiety consisting essentially of a protein that selectively coats and binds to the single-stranded segment, to thereby prepare the biomolecule analyte, wherein the binding moiety coats single-stranded DNA selectively with respect to double-stranded regions.

14. The method of claim 13, wherein the base extension reaction is performed by a DNA or RNA polymerase.

15. The method of claim 13, wherein removing the RNA probes comprises reacting the analyte with a hydroxyl ion.

16. The method of claim 13, wherein the biomolecule analyte is configured for detection of positional information in a nanopore system comprising a nanopore having a diameter from 1 nm to 1 µm.

17. The method of claim 16, further comprising:
generating with the nanopore system a waveform indicative of changes in an electrical property across the nanopore as the biomolecule analyte is translocated therethrough, the changes in the electrical property being indicative of regions including or lacking the binding moiety.

18. The method of claim 13, wherein the biomolecule analyte is configured for detection of positional information in a fluidic channel system comprising a micro-channel having a width from 1 µm to 25 µm, a depth from 200 nm to 5 µm and a length of 1 µm to 10 cm, or a nano-channel having a width from 10 nm to 1 µm, a depth from 10 nm to 1 µm and a length of 1 µn to 10 cm.

19. The method of claim 18, wherein the fluidic channel system includes (i) a pair of detector electrodes positioned perpendicular to the micro- or nano-channel and defining a detection volume therebetween, and (ii) a detector, the detector electrodes being connected to the detector, further comprising:
monitor changes in an electrical property with the detector across the micro- or nano-channel in the detection volume as the biomolecule analyte is translocated between the detector electrodes defining the detection volume, the changes in the electrical property being indicative of regions including or lacking the binding moiety.

20. The method of claim 13, wherein the first plurality of identical, RNA probes is replaced by a pool of RNA probes comprising at least a first plurality of identical, RNA probes and a second plurality of identical, RNA probes, wherein the probes of the second plurality are different from the probes of the first plurality.

21. A method for preparing a biomolecule analyte, said biomolecule analyte comprising a single-stranded human DNA template, at least two identical RNA probes hybridized to the single-stranded DNA template, and a binding moiety coating a portion of the single-stranded DNA template, the method comprising:
   g. providing the single-stranded DNA template;
   h. hybridizing a first plurality of identical RNA probes to the template, each probe having 4 to 12 bases and a 5' end and a 3' end, to thereby form an analyte having at least one single-stranded region and at least one duplex region, the at least one duplex region comprising one of the probes hybridized to a complementary portion of the template;
   i. conducting a base extension reaction in the at least one single-stranded region from the 3' end of the hybridized probe, wherein the base extension reaction comprises adding mononucleotides complementary to the template to extend the duplex region defined by the hybridized probe;
   j. allowing the base-extension reaction to fill each single-stranded region on the analyte;
   k. removing the RNA probes to provide the analyte with at least one single-stranded segment in the region to which an RNA probe had been hybridized; and
   l. reacting the analyte formed in step e with a binding moiety consisting essentially of a protein that selectively coats and binds to the single-stranded segment, to thereby prepare the biomolecule analyte, wherein (i) the binding moiety coats single-stranded DNA selectively with respect to double-stranded regions and (ii) said protein comprises one or more proteins selected from the group consisting of RecA, T4 gene 32 protein, f1 geneV protein, human replication protein A, Pf3 single-stranded binding protein, adenovirus DNA binding protein, and E. coli single-stranded binding protein.

22. A method for preparing a biomolecule analyte, said biomolecule analyte comprising a single-stranded human DNA or human RNA template, at least two identical, oligonucleotide probes hybridized to the single-stranded DNA or RNA template, and a binding moiety coating a portion of the single-stranded DNA or RNA template, the method comprising:
   a. providing the single-stranded human DNA or human RNA template;
   b. hybridizing a first plurality of identical, oligonucleotide probes to the template, each probe having a 5' end and a 3' end, to thereby form an analyte having at least one single-stranded region and at least two duplex regions, each duplex region comprising one of the probes hybridized to a complementary portion of the template, wherein one of the at least one single-stranded regions is disposed between two duplex regions;
   c. conducting a base-extension reaction in the at least one single-stranded region from the 3' end of a hybridized probe abutting the at least one single-stranded region toward the 5' end of an adjacent hybridized probe abutting the at least one single-stranded region, wherein the base extension reaction comprises adding mononucleotides complementary to the template to extend the duplex region defined by the hybridized probe;
   d. terminating the base-extension reaction under termination conditions such that at least one of the remaining single-stranded regions is adjacent to the 5' end of the adjacent hybridized probe; and
   e. reacting the analyte formed in step d with a binding moiety consisting essentially of a protein that selectively coats and binds to the at least one single-stranded portion to thereby prepare the biomolecule analyte, wherein the binding moiety coats single-stranded DNA or RNA selectively with respect to double-stranded regions.

23. A method for preparing a biomolecule analyte, said biomolecule analyte comprising a single-stranded human DNA template, at least two identical RNA probes hybridized to the single-stranded DNA template, and a binding moiety coating a portion of the single-stranded DNA template, the method comprising:
   a. providing the single-stranded human DNA template;
   b. hybridizing a first plurality of identical RNA probes to the template, each probe having a 5' end and a 3' end, to thereby form an analyte having at least one single-stranded region and at least two duplex regions, each duplex region comprising one of the probes hybridized to a complementary portion of the template, wherein one of the at least one single-stranded regions is disposed between two duplex regions;
   c. conducting a base extension reaction in the at least one single-stranded region from the 3' end of the hybridized probe abutting the at least one single-stranded region toward the 5' end of an adjacent hybridized probe abutting the at least one single-stranded region, wherein the base extension reaction comprises adding mononucleotides complementary to the template to extend the duplex region defined by the hybridized probe;
   d. allowing the base-extension reaction to fill each single-stranded region disposed between two duplex regions on the analyte;
   e. removing the RNA probes to provide the analyte with at least one single-stranded segment in the region to which an RNA probe had been hybridized; and
   f. reacting the analyte formed in step e with a binding moiety consisting essentially of a protein that selectively coats and binds to the single-stranded segment, to thereby prepare the biomolecule analyte, wherein the binding moiety coats single-stranded DNA selectively with respect to double-stranded regions.

* * * * *